United States Patent
Shah et al.

(10) Patent No.: US 11,564,931 B2
(45) Date of Patent: Jan. 31, 2023

(54) LOW BENZALKONIUM CHLORIDE BIMATOPROST OPHTHALMIC COMPOSITIONS WITH EFFECTIVE PENETRATION AND PRESERVATION PROPERTIES

(71) Applicant: Somerset Therapeutics LLC, Hollywood, FL (US)

(72) Inventors: Mandar V Shah, Rockaway, NJ (US); Veerappan Subramanian, Warren, NJ (US); Ilango Subramanian, Warren, NJ (US); Aman Trehan, Somerset, NJ (US)

(73) Assignee: SOMERSET THERAPEUTICS, LLC, Hollywood, FL (US)

( * ) Notice: Subject to any disclaimer, the term of this patent is extended or adjusted under 35 U.S.C. 154(b) by 0 days.

(21) Appl. No.: 17/207,346

(22) Filed: Mar. 19, 2021

(65) Prior Publication Data

US 2021/0205327 A1    Jul. 8, 2021

Related U.S. Application Data

(63) Continuation of application No. 17/114,936, filed on Dec. 8, 2020, now abandoned.
(Continued)

(51) Int. Cl.
*A61K 31/5575* (2006.01)
*A61K 31/14* (2006.01)
(Continued)

(52) U.S. Cl.
CPC ........ *A61K 31/5575* (2013.01); *A61K 9/0048* (2013.01); *A61K 9/08* (2013.01);
(Continued)

(58) Field of Classification Search
CPC .. A61K 31/5575; A61K 9/0048; A61K 31/14; A61K 47/26; A61K 47/44
See application file for complete search history.

(56) References Cited

U.S. PATENT DOCUMENTS

| | | |
|---|---|---|
| 6,646,001 B2 | 11/2003 | Hellberg et al. |
| 7,851,504 B2 | 12/2010 | Chang et al. |

(Continued)

FOREIGN PATENT DOCUMENTS

| | | |
|---|---|---|
| WO | 2009013435 | 1/2009 |
| WO | 2009084021 | 7/2009 |

(Continued)

OTHER PUBLICATIONS

Baudouin, et al., "Preservatives in Eyedrops: The Good, the Bad and the Ugly", Progress in Retinal Eye Research. Jul. 2010;29(4):312-34. doi: 10.1016/j.preteyeres.2010.03.001. PMID: 20302969.

(Continued)

*Primary Examiner* — Craig D Ricci
*Assistant Examiner* — Janet L Coppins
(74) *Attorney, Agent, or Firm* — Transformative Legal LLC; Len S. Smith; Denise M. Brown

(57) ABSTRACT

The present invention relates to ophthalmic compositions comprising from 0.005% to 0.02% bimatoprost by weight, less than 100 ppm benzalkonium chloride, and one or more secondary penetration enhancers that detectably enhance(s) penetration of bimatoprost into a mammalian eye such that elevated intraocular pressure is effectively reduced to an extent statistically comparable to compositions comprising higher amounts of bimatoprost and benzalkonium chloride. Further, the invention also provides a process of preparing such compositions and methods of their use for lowering intraocular pressure and treating glaucoma.

13 Claims, 2 Drawing Sheets

Related U.S. Application Data

Figure 1:
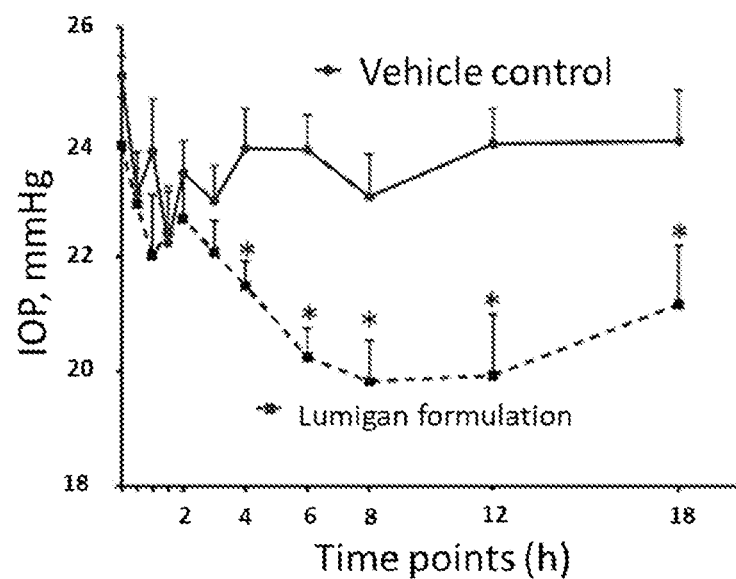

(60) Provisional application No. 62/946,900, filed on Dec. 11, 2019.

(51) Int. Cl.
*A61K 31/165* (2006.01)
*A61K 9/08* (2006.01)
*A61K 47/44* (2017.01)
*A61K 9/00* (2006.01)
*A61K 47/26* (2006.01)
*A61K 47/02* (2006.01)
*A61K 47/12* (2006.01)
*A61K 47/18* (2017.01)

(52) U.S. Cl.
CPC ............ *A61K 31/14* (2013.01); *A61K 31/165* (2013.01); *A61K 47/02* (2013.01); *A61K 47/12* (2013.01); *A61K 47/186* (2013.01); *A61K 47/26* (2013.01); *A61K 47/44* (2013.01)

(56) References Cited

U.S. PATENT DOCUMENTS

| | | | |
|---|---|---|---|
| 8,278,353 | B2 | 10/2012 | Chang et al. |
| 8,299,118 | B2 | 10/2012 | Chang et al. |
| 8,309,605 | B2 | 11/2012 | Chang et al. |
| 8,338,479 | B2 | 12/2012 | Chang et al. |
| 8,343,949 | B2 | 1/2013 | Lyons et al. |
| 8,524,777 | B2 | 9/2013 | Chang et al. |
| 8,586,630 | B2 | 11/2013 | Chang |
| 8,691,802 | B2 | 4/2014 | Lyons et al. |
| 8,772,338 | B2 | 7/2014 | Chang et al. |
| 8,933,120 | B2 | 1/2015 | Chang et al. |
| 8,933,127 | B2 | 1/2015 | Chang et al. |
| 9,155,716 | B2 | 10/2015 | Chang et al. |
| 9,241,918 | B2 | 1/2016 | Chang et al. |
| 10,314,780 | B2 | 6/2019 | Polzer |
| 2013/0005665 | A1* | 1/2013 | Gore ............... A61K 31/568 514/20.5 |
| 2013/0245124 | A1 | 9/2013 | Likitlersuang et al. |
| 2018/0153885 | A1* | 6/2018 | Jain ............... A61K 9/0048 |
| 2018/0228724 | A1* | 8/2018 | Polzer ............... A61K 31/5575 |

FOREIGN PATENT DOCUMENTS

| | | |
|---|---|---|
| WO | 2010102078 | 9/2010 |
| WO | 2012015998 | 2/2012 |
| WO | 2012055571 | 5/2012 |
| WO | 2014138018 | 9/2014 |
| WO | 2016198434 | 12/2016 |
| WO | 2018185788 | 10/2018 |
| WO | 2020178672 | 9/2020 |
| WO | 2021084522 | 5/2021 |

OTHER PUBLICATIONS

Covert D et al. "Adjunctive glaucoma therapy use associated with travoprost, bimatoprost, and latanoprost", Curr Med Res Opin. May 2006;22(5):971-6. doi: 10.1185/030079906x104777. PMID: 16709319.
Day, et al., "Bimatoprost 0.03% Preservative-Free Ophthalmic Solution Versus Bimatoprost 0.03% Ophthalmic Solution (Lumigan) for Glaucoma or Ocular Hypertension: a 12 Week, Randomized, Double-Masked Trial", BMJ Publishing Group, Aug. 2013;97(8):989-93. doi: 10.1136/bjophthalmol-2012-303040.
Eisenberg, D. "Lantanoprost versus bimatoprost", Ophthalmology. 110(9): 1861-1862(2003). DOI:https://doi.org/10.1016/S0161-6420(03)00849-2.
Gandolfi, et al., "Effect of Bimatoprost on Patients with Primary Open-angle Glaucoma or Ocular Hypertension Who are Nonresponders to Latanoprost", American Academy of Ophthalmology. Mar. 2003; 110(3):609-14.
Gandolfi S et al., "Three-Month Comparison of Bimatoprost and Latanoprost in Patients with Glaucoma and Ocular Hypertension", Advances in Therapy May-Jun. 2001;18(3):110-21. doi: 10.1007/BF02850299. PMID: 11571823.
Johnson, et al., "Thermal Stability of Bimatoprost, Latanoprost, and Travoprost Under Simulated Daily Use", Journal of Ocular Pharmacology and Therapeutics, Feb. 2011;27(1):51-9. doi: 10.1089/jop.2010.0115. Epub Nov. 30, 2010. PMID: 21117945; PMCID: PMC3038126.
Hollo G., "The Side Effects of the Prostaglandin Analogues", Expert Opinion on Drug Safety, vol. 6, 2007, Issue 1.
Karslioğlu MZ et al., "Periocular Changes in Topical Bimatoprost and Latanoprost Use", Turkish Journal of Medical Sciences, 2015;45(4):925-30. PMID: 26422869.
Li X et al., "Effects of Latanoprost and Bimatoprost on the Expression of Molecules Relevant to Ocular Inflow and Outflow Pathways", PLoS One. Mar. 24, 2016;11(3):e0151644. doi: 10.1371/journal.pone.0151644. PMID: 27011234; PMCID: PMC4807090.
Ouellette, L.L., "Do Patents Disclose Useful Information?", Harvard Journal of Law & Technology, 25(2) 531-593 (2012).
Parrish, et al., "A Comparison of Latanoprost, Bimatoprost, and Travoprost in Patients with Elevated Intraocular Pressure: A 12-week, Randomized, Masked-evaluator Multicenter Study", American Journal of Ophthalmology. May 2003,135(5):688-703. doi: 10.1016/50002-9394(03)00098-9. PMID: 12719078.
Pillunat, et al., "Preservative-Fee Bimatroprost 0.03% in Patients with Primary Open-Angle Glaucoma or Ocular Hypertension in Clinical Practice", Clinical Opthalmology, Sep. 12, 2016;2;10:1759-65. doi: 10.2147/OPTH.S103084.
Reddy et al., "Tear Biomarkers in Latanoprost and Bimatoprost Treated Eyes", PLoS One. Aug. 6, 2018;13(8):e0201740. doi: 10.1371/journal.pone.0201740. PMID: 30080906; PMCID: PMC6078293.
Sherwood, et al., "Six-Month Comparison of Bimatroprost Once-Daily and Twice-Daily with Timolol Twice-Daily in Patients with Elevated Intraocular Pressure", Survey of Ophthalmology, 2001;45:S361-S368.
Winkler, et al., "Effects of Prostaglandin Analogues on Aqueous Humor Outflow Pathways", Journal of Ocular Pharmacology and Therapeutics, 2014;30(2-3):102-109. doi:10.1089/jop.2013.0179.
Yu M et al., "Travoprost and Latanoprost, but not Bimatoprost, Induced Nausea, Vomiting and Diarrhoea", BMJ Case Rep. 2009;2009:bcr08.2008.0618. doi: 10.1136/bcr.08.2008.0618. Epub Feb. 26, 2009. PMID: 21686721; PMCID: PMC3028105.
European Medicines Agency in a 2019 report, around 74% of ophthalmic preparations comprise BKC (see https://www.ema.europa.eu/en/documents/report/benzalkonium-chloride-used-excipient-report-published-support-questions-answers-benzalkonium_en.pdf).
LUMIGAN® Canadian Product Monograph, available at https://allergan-web-cdn-prod.azureedge.net/allergancanadaspecialty/allergancanadaspecialty/media/actavis-canada-specialty/en/products/0060-lumigan-rc-product-monograph-english.pdf).

\* cited by examiner

LOW BENZALKONIUM CHLORIDE BIMATOPROST OPHTHALMIC COMPOSITIONS WITH EFFECTIVE PENETRATION AND PRESERVATION PROPERTIES

CROSS-REFERENCE TO RELATED PATENT APPLICATIONS

This application is a continuation of and claims priority to presently co-pending U.S. patent application Ser. No. 17/114,936, filed Dec. 8, 2020, entitled Low Benzalkonium Chloride Bimatoprost Ophthalmic Compositions with Effective Penetration & Preservation Properties, which claims the benefit of priority to U.S. Patent Application No. 62/946,900, filed Dec. 11, 2019, entitled Bimatoprost Ophthalmic Composition. The entirety of both referenced priority applications is hereby incorporated by reference.

FIELD OF THE INVENTION

The current invention relates generally to pharmaceutical compositions suitable for ophthalmic applications. More specifically, the current invention relates generally to ophthalmic compositions comprising bimatoprost and methods of their production and use.

BACKGROUND OF THE INVENTION

Glaucoma is a widespread, sight-threatening disease usually associated with an elevated intraocular pressure (IOP) that, if not treated properly, potentially causes irreversible optic nerve and visual field damages. Management of the disorder requires life-long treatment, usually by application of eye drops.

A large range of eye drops, containing beta-blockers, alpha-2 agonists, carbonic anhydrase inhibitors, and prostaglandins, are available for treating glaucoma, and for more than 20 years, prostaglandin analogues (also simply called "prostaglandins") have been successfully used as a first-line treatment in glaucoma patients. Developed and marketed prostaglandins used in treatment of eye conditions include latanoprost (initially developed and sold under the brand name XALATAN™), travoprost (sold as, e.g., TRAVATAN Z™), tafluprost (sold as, e.g., ZIOPTAN™), and bimatoprost (developed and sold under the brand name LUMIGAN®).

Despite overlapping or similar functions and properties, the prostaglandins have been repeatedly demonstrated to exhibit significant differences at both biological/cellular and physiological level effects, such as with respect to irritation and other adverse effects. For example, pharmacologic and pharmacokinetic data suggest the existence of a unique bimatoprost receptor, distinct from the known FP receptors; however, this receptor is yet to be cloned and bimatoprost has not been shown to work independent of FP receptor activation. Winkler N S et al. J Ocul Pharmacol Ther. 2014; 30(2-3):102-109. doi:10.1089/jop.2013.0179. Another study reports that bimatoprost appears to reduce the IOP of patients who are unresponsive to latanoprost, suggesting that the prostamide bimatoprost and the FP receptor agonist latanoprost stimulate different receptor populations. Gandolfi S A, Cimino L. Ophthalmology. 2003 March; 110(3): 609-14. Cytokine expression studies relating to prostaglandins have also evidenced that these compounds stimulate different cytokine pathways. For example, MMP-9 expression was higher in eyes receiving latanoprost while the MMP-2 expression was higher in eyes receiving bimatoprost with MMP1 protein levels being higher in the former. Reddy S et al. PLoS One. 2018 Aug. 6; 13(8):e0201740. doi: 10.1371/journal.pone.0201740. PMID: 30080906; PMCID: PMC6078293. Differences in fibronectin expression and in aquaporin-1 expression in response to bimatoprost as compared to latanoprost also has been linked to variability in the IOP-lowering efficacy in some studies. Li X et al. PLoS One. 2016 Mar. 24; 11(3):e0151644. doi: 10.1371/journal.pone.0151644. PMID: 27011234; PMCID: PMC4807090. In terms of distribution, bimatoprost has been shown to reach target tissues differently than latanoprost and findings of intact bimatoprost in the target ciliary body indicated its direct involvement in reducing IOP, and bimatoprost has been linked with poor corneal penetration when compared to latanoprost and travoprost. Eisenberg, D. Ophthalmology. 110(9): 1861-1862 (2003). Topical bimatoprost therapy also causes more periocular changes than latanoprost therapy. Karslioğlu M Z et al. Turk J Med Sci. 2015; 45(4):925-30. PMID: 26422869. Prostaglandin products also are associated with differences in terms of active pharmaceutical ingredient (API) stability. Bimatoprost has been shown to remain stable under conditions where latanoprost and travoprost undergo degradation. Johnson T V et al. J Ocul Pharmacol Ther. 2011 February; 27(1):51-9. doi: 10.1089/jop.2010.0115. Epub 2010 Nov. 30. PMID: 21117945; PMCID: PMC3038126.

The prostaglandins also exhibit clinical differences. For example, fewer latanoprost-treated patients reported ocular adverse events (P<0.001, latanoprost vs bimatoprost), fewer reported hyperemia (P=0.001, latanoprost vs bimatoprost), and average hyperemia scores were lower at week 12 (P=0.001, latanoprost vs bimatoprost). While latanoprost, bimatoprost, and travoprost have in some studies been shown to be comparable in their ability to reduce IOP in OAG and OH patients, latanoprost exhibited greater ocular tolerability. Parrish R K et al. Am J Ophthalmol. 2003 May; 135(5):688-703. doi: 10.1016/s0002-9394(03)00098-9. PMID: 12719078. That said, nausea, vomiting and sometimes diarrhea should be considered as adverse effects of travoprost and latanoprost. In this report, bimatoprost did not induce the same gastrointestinal adverse effects, probably due to its different chemical structure and receptors. Yu M et al. BMJ Case Rep. 2009; 2009:bcr08.2008.0618. doi: 10.1136/bcr.08.2008.0618. Epub 2009 Feb. 26. PMID: 21686721; PMCID: PMC3028105. Conjunctival hyperemia is more commonly associated with bimatoprost therapy, while headache was more frequent with latanoprost. Gandolfi S et al. Adv Ther. 2001 May-June; 18(3):110-21. doi: 10.1007/BF02850299. PMID: 11571823. However, bimatoprost provided lower mean pressures than latanoprost at every time point when studied and was statistically superior in achieving low target pressures. Id. Patients using travoprost or bimatoprost have been shown to have a significantly lower rate of adjunctive medication use compared to patients starting on latanoprost monotherapy (22.5%, 23.2%, and 30.2%, respectively), reflecting differences in overall efficacy of prostaglandins. Covert D et al. Curr Med Res Opin. 2006 May; 22(5):971-6. doi: 10.1185/030079906x104777. PMID: 16709319.

Bimatoprost specifically is classified as prostamide and a synthetic analogue of prostaglandin $F_{2\alpha}$ ($PGF_{2\alpha}$) with potent ocular hypotensive activity. Its chemical name is (Z)-7-[(1R, 2R, 3R, 5S)-3, 5-Dihydroxy-2-[(1E, 3S)-3-hydroxy-5-phenyl-1-pentenyl] cyclopentyl]-5-N-ethylheptenamide, and its molecular weight is 415.58. Its molecular formula is $C_{25}H_{37}NO_4$. The chemical structure of bimatoprost is:

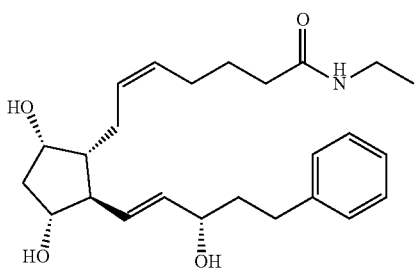 [SMILES: CCNC(=O)CCC/C=C\C[C@@H]1[C@@H](/C=C/[C@@H](O)CCc2ccccc2)[C@H](O)C[C@@H]1O]

Bimatoprost lowers IOP in patients with glaucoma or ocular hypertension by increasing outflow of aqueous humor through both the trabecular meshwork and uveoscleral routes.

In 2001, the FDA approved LUMIGAN®, a sterile ophthalmic solution containing 0.03% bimatoprost ("LUMIGAN® 0.03%") developed by ALLERGAN, a leading, global ophthalmologic pharmaceutical company. The formulation of LUMIGAN® 0.03% contains benzalkonium chloride ("BKC") 0.05 mg/mL (50 ppm). The formulation also includes sodium chloride; sodium phosphate, dibasic; citric acid; and purified water. Sodium hydroxide and/or hydrochloric acid may be added to adjust pH. The pH during LUMIGAN® 0.03%'s shelf life ranges from 6.8-7.8. The product is indicated for the reduction of elevated intraocular pressure in patients with open angle glaucoma or ocular hypertension.

LUMIGAN® 0.03% became a successful product, with 2011 sales of more than $600 million US dollars. However, LUMIGAN® 0.03% was known to also cause hyperemia (eye redness) that led many patients to discontinue use of the product. Vasodilatation in the conjunctiva, the most frequent adverse effect, led to about 3% of patients discontinuing therapy. See, e.g., Sherwood M, et al. Sury Ophthalmol. 2001; 45:S361-S368 and Hone) G. Exper Opin Drug Saf. 2007; 6:45-52. An increasing body of research also pointed to BKC causing ophthalmological side effects. In fact, BKC was reported to consistently demonstrate toxic effects in laboratory, experimental, and clinical studies, causing tear film instability, loss of goblet cells, conjunctival squamous metaplasia and apoptosis, disruption of the corneal epithelium barrier, and damage to deeper ocular tissues. Baudouin C et al. Prog Retin Eye Res. 2010 July; 29(4):312-34. doi: 10.1016/j.preteyeres.2010.03.001. PMID: 20302969. Such issues led to the conclusion that "Care should therefore be taken to avoid the long-term use of preservatives, otherwise a less toxic alternative to benzalkonium chloride should be developed, as this weakly allergenic but highly toxic compound exerts dose- and time-dependent effects." Id. The authors further reported "On the basis of all these experimental and clinical reports, it would be advisable to use benzalkonium-free solutions whenever possible . . . " Id. Patients can experience hypersensitivity reactions with BKC and BKC may be absorbed by soft contact lenses creating challenges for contact lens users.

In 2009, the European Medicines Agency's Committee for Medicinal Products for Human Use concluded that unpreserved formulations "are needed for patients with lower tolerance to preservatives," and "for long-term treatment, formulations without preservatives are valuable alternatives." Around this time (in 2011), the first preservative-free (PF) latanoprost formulation (Monoprost®; Laboratoires Thea, Clermont-Ferrand, France) was made available. Allergan similarly developed and conducted large-scale clinical trials with a preservative-free (and, thus, BKC-free) bimatoprost formulation ("Bimatoprost PF"). Bimatoprost PF study results led to the conclusion that the product candidate was "non-inferior and equivalent to bimatoprost in its ability to reduce IOP-lowering with a safety profile similar to bimatoprost." Day D G. Br J Ophthalmol. 2013 August; 97(8):989-93. doi: 10.1136/bjophthalmol-2012-303040. Follow up studies with 0.03% PF bimatoprost formulations also were associated with positive clinical results. Pillunat L E. Clin Ophthalmol. 2016 Sep. 12; 10:1759-65. doi: 10.2147/OPTH.S103084.

However, Allergan did not develop a PF bimatoprost product. Rather, in 2010, the FDA approved LUMIGAN® 0.01%, which has only one third the amount of active ingredient, but four times the amount of BKC as LUMIGAN® 0.03% (i.e., 0.2 mg/mL (200 ppm) BKC). Surprisingly, LUMIGAN® 0.01% was demonstrated in large-scale trials to have similar efficacy to LUMIGAN® 0.03%, viz., IOP-lowering within 0.5 mmHg of that of LUMIGAN® 0.03%, despite the significant reduction in API, but LUMIGAN® 0.01% caused less frequent and severe hyperemia than LUMIGAN® 0.03%. Allergan studies with bimatoprost formulations comprising 200 ppm BKC (like LUMIGAN® 0.01%) were associated with an about 375% increase in bimatoprost permeability in a rabbit corneal epithelial cell layer model (See LUMIGAN® Canadian Product Monograph.

A very large number of patent documents disclose bimatoprost formulations containing some amount of BKC. While some of these disclosures provide actual data or specific disclosures a number of these patent references provide non-specific broad disclosures that likely are not supported by any experimental support. In this respect it is worth remembering that patent examiners generally focus on a patent's claims, rather than assessing the scientific validity of the patent's disclosure, resulting in later recognition of serious flaws in patent data and scientific reasoning, which patent owners are "under no obligation to retract or correct." Piehler, D. Legal and practical pitfalls in making use of patents. Nature 462, 276 (2009). Indeed 40% of researchers do not rely on patent information and a larger number point to the lack of credibility in patent disclosures, particularly those disclosures lacking technical detail. Ouellette, L. L., Harvard Journal of Law & Technology, 25(2) 531-593 (2012). Nonetheless, such patent references are disclosed below for purpose of describing the background art in detail.

U.S. Pat. No. 6,646,001 discloses compositions allegedly comprising 0.03% bimatoprost and 0.01% benzalkonium chloride or "0.01%+5% excess" benzalkonium chloride.

U.S. Pat. No. 7,851,504 describes compositions allegedly comprising from 0.005% to 0.02% bimatoprost by weight and from 100 ppm to 250 ppm BKC. The '504 patent teaches that the bimatoprost formulations with 100 ppm to 250 ppm of benzalkonium chloride (BKC) resulted in higher permeability, whereas formulations containing less than the lower amount of BKC or formulations containing d-alpha tocopherol polyethylene glycol 1000 succinate (TPGS) resulted in decreased bimatoprost permeability compared to bimatoprost formulations with 100 ppm to 250 ppm of BKC.

U.S. Pat. No. 8,933,120 discloses an ophthalmic composition comprising about 0.01%-0.015% w/v bimatoprost and about 0.02% w/v benzalkonium chloride. U.S. Pat. Nos. 7,851,504; 8,338,479; 8,309,605 and 8,586,630 disclose compositions comprising about 0.01% bimatoprost, about 200 ppm benzalkonium chloride, a phosphate buffer, citric acid monohydrate, sodium chloride, ethylenediaminetetraacetic acid, water and having a pH of about 7.3 and its use for treating glaucoma or intraocular hypertension.

U.S. Pat. No. 9,241,918 discloses an ophthalmic composition for the treatment of glaucoma or elevated intraocular pressure comprising about 0.01% w/v bimatoprost, about 200 ppm benzalkonium chloride, about 0.268% w/v dibasic sodium phosphate heptahydrate, about 0.014% w/v citric acid monohydrate, about 0.81% w/v sodium chloride, and water.

U.S. Pat. Nos. 8,343,949 and 8,691,802 disclose a composition comprising 0.03% bimatoprost, 0.39% sodium chloride, 0.6% boric acid, 0.045% sodium borate, 0.014% citric acid monohydrate, 0.5% carboxymethylcellulose, and 0.005% stabilized chlorine dioxide, wherein the pH is adjusted to 7.3 by the addition of hydrochloric acid or sodium hydroxide. It also discloses an ophthalmic composition consisting of about 0.03% bimatoprost, about 0.01% Purite™, about 0.268 sodium phosphate dibasic, about 0.014% citric acid, about 0.83% sodium chloride, HCl/NaOH and purified water. WO 2009/013435 discloses additional types of 0.03% bimatoprost formulations including formulations comprising 0.02%, 0.005%, or 0.01% BKC. WO2012015998 similarly describes 0.03% bimatoprost formulations. WO2012055571 also discloses formulations comprising bimatoprost and BKC (0.02% or 0.05 mg/mL). WO2014138018 discloses 0.03% bimatoprost formulations comprising 50 ppm BKC.

U.S. Patent Publication No. 20130245124 is an Allergan patent application that discloses compositions allegedly comprising 0.03% bimatoprost that are free of preservatives. All patent applications in the family are now withdrawn and, as noted already, Allergan elected not to develop a preservative free bimatoprost formulation, despite significant pressure in the industry.

WO2010102078 (related to U.S. Pat. Nos. 8,278,353, 8,299,118, 8,933,127; 8,524,777, 8,772,338, and 9,155,716) is another Allergan patent application that broadly discloses formulations comprising 0.005% to 0.02% bimatoprost by weight and from 100 ppm to 250 ppm BKC. Experimental data in the '078 PCT application includes a comparison of various bimatoprost formulations containing amounts of BKC versus bimatoprost formulations containing d-α-tocopherol polyethylene glycol 1000 succinate (TPGS), a water-soluble nonionic surfactant and penetration enhancer. The results of this study demonstrated that 50 ppm BKC outperformed any concentration of TPGS in terms of bimatoprost aqueous humor concentration in an animal model and that 200 ppm BKC far outperformed 50 ppm BKC (see FIG. 1 and related discussion). Additional studies in corneal cell cultures also demonstrated that higher levels of BKC were associated with significantly higher amounts of corneal cell penetration (see FIG. 2 and associated discussion). The '078 PCT application, for example, states "0.03% Bimatoprost containing 200 ppm BKC resulted in 57% higher aqueous humor AGN 191522 concentration compared to Bimatoprost (50 ppm BKC)." Consistent with other Allergan studies reported above, clinical studies reported on or described in the '078 PCT conclude that "bimatoprost 0.01% (200 ppm BKC) had superior safety and similar efficacy to LUMIGAN® (0.03%, 192024-030)."

WO2016198434 (related to, e.g., U.S. Pat. No. 10,314,780) is directed to "drippable" ophthalmic gel formulations. The '434 PCT application discloses formulations comprising a broad range of bimatoprost (0.003 to 0.03% by weight). Specific exemplary gels in the '434 PCT application were either BKC-free or contained 0.02% BKC or 0.005% BKC in combination with polyacrylate (Carbomer) and povidone (PVP). Other drippable formulations described in the '434 PCT application also or alternatively include poly(vinyl)alcohol, dextran, polyethylene glycol, or carboxymethyl cellulose in combination with polyacrylate. AUC values for such formulations were shown to be around four times as high as the AUC-values of LUMIGAN® formulations. Formulations with PVP had AUC values significantly higher than with poly(vinyl)alcohol. Formulations containing polysorbate80 were tested but did not appear to show significantly beneficial differences from formulations lacking polysorbate80. BKC containing formulations outperformed BKC formulations. Of course, the gel formulations of the '434 PCT application are expected to have significantly different use characteristics as compared to ophthalmological solutions, such as LUMIGAN® 0.01% and LUMIGAN® 0.03%.

WO2018185788 describes BKC-free bimatoprost formulations with improved bioavailability. The disclosure describes formulations containing bimatoprost or its pharmaceutically acceptable salt in an amount ranging from about 0.005% to 0.015% weight by volume; a biguanide compound present in an amount ranging from about 0.003% to 0.05% weight by volume; and an acylated amino acid present in an amount ranging from about 0.01% to 0.1% weight by volume. The '788 PCT application repeatedly touts the advantages of a BKC free formulation.

WO2009/084021 describes formulations comprising a variety of prostaglandins, including latanoprost, travoprost, and "prostaglandin derivatives" generally. In one passage, the '021 PCT application describes formulations comprising 0.00001% w/v to about 0.2% w/v bimatoprost. The '021 PCT application provides no clinical or preclinical data to support this incredibly broad and seemingly non-credible claim. The only specific bimatoprost example provided in the '021 PCT application actually discloses 0.03% bimatoprost, the same amount as contained in LUMIGAN® 0.03%.

WO2020178672 similarly describes a very diverse variety of bimatoprost formulations, including formulations containing 0.01% bimatoprost, combined with a large number of different types of excipients not in LUMIGAN® (e.g., benzododecinium bromide, boric acid, and glycerin). However, the '672 PCT application appears to lack any preclinical or clinical data associated with any of the various proposed formulations listed therein. The '672 PCT application states, "The object of the present invention is to provide an alternate pharmaceutical composition of bimatoprost which is free of phosphate buffer" (although the disclosure of the '672 PCT application appears to describe both phosphate buffer-containing compositions and phosphate buffer-free compositions). The '672 PCT application also describes BKC-free compositions as well as compositions comprising "less than 0.02% benzalkonium chloride." However, all specific examples of formulations provided in the '672 PCT application either disclose BKC-free formulations or formulations containing 0.02% BKC, the same amount as used in LUMIGAN® 0.01%. Thus, the '672 PCT application's mention of formulations comprising "less than 0.02%" BKC appears to be based on unreliable conjecture or is only a patent drafting artifact.

Despite this significant amount of patent document disclosures, there is remarkably little reported in scientific literature concerning bimatoprost formulations other than LUMIGAN® 0.01% and LUMIGAN® 0.03% and there remains a lack of effective alternative options in the market to these products. Clearly, the extensive amount of experimentation and conjecture in this field evidence that an application of inventive ingenuity will be required to develop effective alternative bimatoprost formulations having properties that address the several competing concerns that exist around LUMIGAN® products.

Principles of Construction & Abbreviations

The following principles are applicable to interpreting the disclosure provided here. These principles apply unless clearly contradicted by express statement, context, or plausibility.

For sake of conciseness, well-known symbols are used in places herein. For example, ("e.g.,") The symbols >, ≥, ≤ and < are given their ordinary meaning (e.g., >1 means "greater than 1", <2 means "less than 2," e.g., >2 Xs means "more than two Xs," "≤" means "less than or equal to" and "≥" means "greater than or equal to") A slash "/" can indicate "or" (A/B means A or B) or can indicate an element with 2 names.

Terms in the singular implicitly convey corresponding disclosure of the plural and vice versa (e.g., a passage referring to use of an element implicitly discloses the corresponding use a plurality of such elements). The terms "a," "an," "the," and similar referents likewise refer to both the singular & the plural of the associated element (e.g., "an X" means "one or more Xs"). The inclusion of "(s)" after an element indicates that one or more of such an element is present, performed, and the like.

Terms such as "here" and "herein" means "in this disclosure."

In the absence of other definition or understanding in the art, the term "some" with respect to elements of a method or composition means "2 or more" and with respect to a part of a whole means "at least 5%" (i.e., ≥5%). The phrase "one, some, most, generally all (i.e., at least 75%), or all," is used in a manner such that each of is an independent aspect of the described feature.

"Significant", as used in the phrase "detectable or significant" (or "detectably or significantly") means results that are statistically significant using an appropriate test in the given context (e.g., p≤0.05/0.01).

Lists of elements can be employed for conciseness. Unless indicated, each member of each list is an independent aspect of the invention.

Ranges of values are used to concisely refer to each value in the range and within an order of magnitude of the range endpoints without having to explicitly write each value. E.g., a recited range of 1-2 implicitly discloses each of 1.0, 1.1, 1.2, 1.3, . . . 1.8, 1.9, and 2.0 & a recited range of 10-20 is to be interpreted as implicitly providing support for each of 10, 11, 12, 13, . . . 19, and 20. All recited ranges include the end points of the provided range, regardless of how the range is described, unless the exclusion of such endpoints is clearly indicated, regardless of the terminology used to describe the range. E.g., a range "between 1 & 5" will include 1 and 5 in addition to 2, 3, and 4 (and all numbers between such number within an order of magnitude of such endpoints and within such endpoints, in this example 1.1 and 4.9).

Terms of approximation, e.g., "about" or "approximately" are used to conveniently refer to a range of closely related values or where a precise value is difficult to measure or measurement difficult to define. The scope of value modified by a term of approximation will depend on the context of the disclosure or understanding of (a) person of ordinary skill in the art. Absent such guidance, terms such as "about" should be understood as meaning +/−10% of the indicated value(s). All exact values provided herein are representative of corresponding approximate values and vice versa (e.g., all exact exemplary values provided with respect to a particular factor or measurement can be considered to also provide a corresponding approximate measurement, modified by "about", e.g., disclosure of "about 10" implicitly discloses both 10 exactly and 9-11). Ranges described with one or more approximate numbers should be interpreted as indicating that all endpoints and other relevant values encompassed by the range may be similarly described, regardless of any different presentations included in TD (e.g., "about 10-20" should be interpreted in the same manner as "about 10-about 20").

Use of the term "or" herein is not meant to imply that alternatives are mutually exclusive. In other words, "or" means "and/or." The occasional explicit use of "and/or" herein has no effect on this interpretation of "or." The scope of "or" meaning "and/or" in a phrase such as "A, B, and/or C" implicitly supports each of: A, B, and C; A, B, or C; A or C; A or B; B or C; A and C; A and B; B and C; A (alone); B (alone); and C (alone). The term "also" means "also or alternatively".

Any reference to "combination" or "combinations" of listed elements means combination(s) of any or all thereof.

No claim here is meant to be interpreted under "means-plus-function" construction unless such intent is clearly indicated by use of the terms "means for" or "step for." Terms such as "configured to" or "adapted to" are not intended to suggest a "means-plus-function" interpretation, but, rather, indicate an element is configured to, designed to, selected to, or adapted to achieve a certain performance, characteristic, property, or the like using the principles described herein and/or generally known in the art.

"Appreciably comprises" means ≥1% of a composition, component, or collection is composed of a referenced element. The phrase "appreciably associated" means ≥1% of an element is AW another element.

"Materially comprises" means ≥5% of the composition, component, or collection is/is made of the subject element. Phrases such as "materially associated" and "in material part" should be similarly interpreted.

"Considerably comprises" means that ≥20% of a composition, component, or collection is/is made of referenced element.

"Predominately comprises" means "most," i.e., more than ½ (i.e., >50%) of a feature (e.g., a composition or a population).

"Generally consists of" and similar phrases such as "generally is," "generally are," "generally most," "generally all," "generally," or "generally is composed of" means that ≥75% of the composition, collection, or component is or is made up of the referenced element.

"Substantially consists of" means ≥90% of the referenced composition, collection, or component is made up of the referenced element. "Substantially associated" means that ≥90% of a referenced item is AW a second item. Phrases like "substantially all," "nearly all," and "nearly entirely," should be similarly construed.

Phrases such as "consists essentially of" or "essentially" with respect to a step/element means that any step/element that maintains the fundamental features of the referenced element/step or retains the desired function of such element/step. The fundamental features and functions of elements and steps will be clear to a person having ordinary skill in the art from the disclosure in view of the art. Where features and functions are not clear, any such phrase should be interpreted as meaning "substantially consists of."

Elements that "consist of" a step/element are limited to the step or element, within bounds of detection and as practically construed in the art. The terms "including", "containing", and "having" should be interpreted openly herein, e.g., as meaning "including, but not limited to", "including, without limitation", or "comprising", unless otherwise such a meaning is clearly contradicted. Terms such as "comprising", "having", "including", or "containing" should be similarly construed when applied to the performance of a step, e.g., comprising means including any detectable amount of an element or including any detectable performance of a step.

A description of any aspect of the invention using terms such as "comprising" or similar term (e.g., "including") with respect to a step/element simultaneously implicitly discloses corresponding aspects of the invention that (1) appreciably comprise the step/element, (2) materially comprise the step/element, (3) considerably comprise the step/element, (4) predominately comprise (otherwise referred to as "mostly" or "primarily" comprises) the step/element, (5) generally consists of the step/element (or is "generally adapted" to, is "generally composed" of, "generally is," "generally only" is/are, "generally are," the element, and the like), or (6) substantially consists of (or "substantially is" or "substantially only" is/are) the step/element, (7) consists essentially of the element/step, or (8) consists of the step/element (or "only is" or "only contains"). E.g., disclosure of a composition comprising "element X" correspondingly implicitly discloses compositions that appreciably, materially, considerably, or predominately comprise, and generally, substantially, essentially, or only/completely consist of or CO) element X.

Changes to tense or presentation of phrases defined herein (e.g., using "comprises predominately" instead of "predominately comprises") do not modify the meaning of the defined phrase.

As used herein, the term "formulation" or "formulations" can be used synonymously with "composition" or "compositions". For example, an aspect describing one or more characteristics of a formulation of the invention also describes one or more characteristics of the invention when the invention is referred to as a composition. Both terms are used herein to refer to the combination of ingredients providing the characteristics of a final product (e.g., in terms of efficacy, stability, and/or side effects, etc.) described herein.

All references, including publications, patent applications, and patents, cited herein, including patents and patent applications cited above, are hereby incorporated by reference to the same extent as if each reference were individually and specifically indicated to be incorporated by reference and were set forth in its entirety herein. Accordingly, the reader should review and consider such references in understanding the full content of this disclosure. E.g., unless clearly contradicted by context or explicit statement, the disclosure of such documents relating to formulations, methods of production, and methods of use of compositions and devices can be combined with the teachings provided herein to provide additional useful compositions and applications. However, the reader should understand that the citation and incorporation of patent documents herein is limited to the technical disclosure of such patent documents and does not reflect any view of the validity, patentability, and/or enforceability of such patent documents. Moreover, in the event of any conflict between this disclosure and the teachings of such documents, the content of this disclosure will control with respect to properly understanding the various aspects of the invention. Numerous references have been included in this disclosure to incorporate information available from other sources that illustrate the scope of the invention or aid in putting aspects of it into practice. While efforts have been made to include the most relevant references for such purposes, readers will understand that not every aspect of every cited reference will be applicable to the practice of the invention.

All headings and sub-headings (e.g., "Principles of Construction") are used for convenience only and do not limit the scope of any aspect of the invention. Aspects of the invention described under a heading can apply or combine with other aspects of the invention.

Numerous examples and aspects are provided here to exemplify and clarify the invention. No example, aspect, or combination or pattern thereof is intended to pose a limitation on the scope of the invention. In general, aspects of the invention should not be limited to any particular provided exemplary processes, compositions, or methodologies. All methods described herein can be performed in any suitable order unless otherwise indicated herein or otherwise clearly contradicted by context or plausibility. Unless clearly indicated or contradicted by context or plausibility, the elements of a described composition, device, or method can be combined in any suitable manner and by any suitable method and any combination of the various elements, steps, components, or features or variations thereof are aspects of the invention.

No part of this specification should be construed as indicating any element or step is essential to the practice of the invention unless as much is explicitly stated. Unless expressly otherwise indicated, description of terms known in the art is for exemplifying versions or embodiments only and not intended to limit the scope of any aspect of the invention. Unless defined otherwise, technical and scientific terms used herein have the same meanings as commonly understood by persons of ordinary skill in the art and implicitly comprise the broadest interpretation based on such usage as well as any narrower interpretation(s) based on specific descriptions provided. In general, any methods and materials similar or equivalent to those described can be used in the practice or testing of embodiments of the invention, methods, devices, and materials described herein.

Unless otherwise indicated, compositions specifying a percentage are by weight unless a different value would be understood in the art. If a variable is not accompanied by a value, any previously provided value typically applies.

SUMMARY OF THE INVENTION

This invention provides new formulations and associated new methods for treating elevated intraocular pressure (e.g., such as elevated intraocular pressure associated with glaucoma). Any of the aspects described under this section can be combined with any other aspect described in this section or with any other aspect of this disclosure.

In certain respects, the invention provides compositions and methods for treating elevated intraocular pressure (e.g., such as elevated intraocular pressure associated with glaucoma), via formulations comprising a reduced amount of benzalkonium chloride than presently available formulations such as Allergan's LUMIGAN® 0.01% and, in some aspects, LUMIGAN® 0.03%.

In aspects, formulations of the invention are compositions comprising between about 0.005% to 0.02% of a bimatoprost compound by weight, benzalkonium chloride in an amount of between about 0.003 to about 0.007% by weight (or less than 100 ppm), and further comprising an effective amount of at least one secondary penetration enhancer that detectably enhances penetration of the bimatoprost into a mammalian eye.

In aspects, administration of effective amounts of the compositions of the invention results in a reduction of intraocular pressure in a treated mammalian eye that is at least statistically comparable to the same amount of a composition comprising the same amount of bimatoprost compound and at least about 200% more benzalkonium chloride.

In certain facets, the formulations of the invention are liquid solutions administered as drops to the mammalian eye once to twice per 24-hour period. In aspects administration of the formulated compositions of the invention result in a detectably or significantly greater reduction in intraocular pressure than LUMIGAN® 0.01% (e.g., the formulation of LUMIGAN® 0.01% as presented in Table 1) as measured 2-18 hours after administration to the mammalian eye.

According to some embodiments, the formulations of the invention are capable of reducing intraocular pressure in a mammalian eye suffering from increased intraocular pressure by at least an average of about 1% more than LUMIGAN® 0.01% when measured in a statistically significant population of mammals in an appropriately powered and administered study, and are further capable of maintaining the stability of bimatoprost (e.g., to within 10% of that of the initial concentration of bimatoprost) when stored up to at least 3 months at 40° C. and 25% RH, at 25° C. and 40% RH, or both, when measured in an appropriately conducted stability study, without the induction of bimatoprost impurities above acceptable limits.

In some aspects, the invention describes formulations comprising low concentrations of bimatoprost, low concentrations of BKC, and the at least one secondary penetration enhancer which makes up at least about 0.2% of the composition. In some facets, the secondary penetration enhancer(s) of the formulations of the invention comprise at least one additional ophthalmologically suitable quaternary ammonium salt, selected from a group comprising benzethonium chloride, benzyltrimethylammonium chloride, lauryl trimethyl ammonium chloride, or any combination thereof. In aspects, the formulations are free of secondary penetration enhancer(s) comprising a quaternary ammonium salt.

In aspects, the formulations of the invention comprise a secondary penetration enhancer characterizable as a non-ionic surfactant and emulsifier, clear in aqueous solution, non-irritating to ocular tissue, and is capable of increasing the penetration of bimatoprost within ocular tissue, including any such compound modified in such a way that does not lead to a detectable or significant difference with respect to some, most, or generally all such characteristics with respect to an amount of polysorbate 80 that achieves a statistically similar level of penetration of bimatoprost.

In one facet, the invention comprises formulations wherein the at least one secondary penetration enhancer comprises one or more ophthalmologically suitable polyoxyethylene sorbitan fatty acid esters; in certain further facets the formulations comprise polysorbate 20, polysorbate 80, or both. In some aspects the formulations of the invention comprise one or more secondary penetration enhancers which are composed of, consist of, or consist essentially of polysorbate 80.

In certain aspects, the invention provides formulations and methods for reducing intraocular pressure, such as, e.g., reducing intraocular pressure associated with glaucoma, by reducing the amount of benzalkonium chloride, a potentially toxic preservative as described above, and incorporating one or more non-toxic compounds such as polysorbate 80. In aspects, the invention provides formulations and methods capable of achieving a comparable, detectably improved, or significantly improved level of intraocular pressure reduction using 50 ppm of benzalkonium chloride, as compared to LUMIGAN® 0.01%, containing 200 ppm of BKC.

According to some embodiments, the formulations of the invention comprise secondary penetration enhancer(s) comprising one or more ophthalmologically suitable non-ionic surfactant having an HLB value of at least 14.5, such as, e.g., at least 16.5. In aspects, the secondary penetration enhancer of the formulations of the invention are selected from a group comprising a polyoxyl-n-castor oil, a polyoxyethylene, a polyoxypropylene, and/or any combination or block polymer thereof.

In one aspect, the invention describes formulations having any one of more characteristics described above and further which comprise a tertiary penetration enhancer. In aspects, such a tertiary penetration enhancer is selected from a group comprising compounds characterizable as a castor oil, a polyethylene glycol such as tocopherol polyethylene glycol succinate (TPGS), or comprises tromethamine.

According to certain embodiments, the invention is a method of reducing elevated intraocular pressure in a mammal comprising administering an effective amount of any one or more ophthalmologically suitable compositions described above, alone or in combination with one another. Further, in certain embodiments, the invention is a method of producing any one or more of the ophthalmologically suitable compositions described above. In aspects, the formulations of the invention, the application of the method, or both is/are capable of providing substantially equivalent or improved efficacy in reducing intraocular pressure while: reducing hyperemia (e.g., conjunctival hyperemia); reducing tear film instability; reducing loss of goblet cells; reducing conjunctival squamous metaplasia and apoptosis; reducing disruption of the corneal epithelium barrier; reducing damage to deep ocular tissue; reducing hypersensitivity reactions; reducing other known ocular side effects known to be caused by the active bimatoprost, benzalkonium chloride, or the combination thereof; reducing absorption of BKC by soft contact lenses; maintaining users on a longer course of therapy; or any combination thereof, than similar formulations, similar methods comprising similar formulations with comparable intraocular pressure reduction capability, or formulations having higher BKC concentration, formulations having higher bimatoprost concentration, or any combination thereof.

BRIEF DESCRIPTION OF THE DRAWINGS/FIGURES

FIG. 1 presents the effect of LUMIGAN® 0.01% in reducing IOP in a steroid-induced ocular hypertension rat model, as determined by a controlled study.

Figure 2:
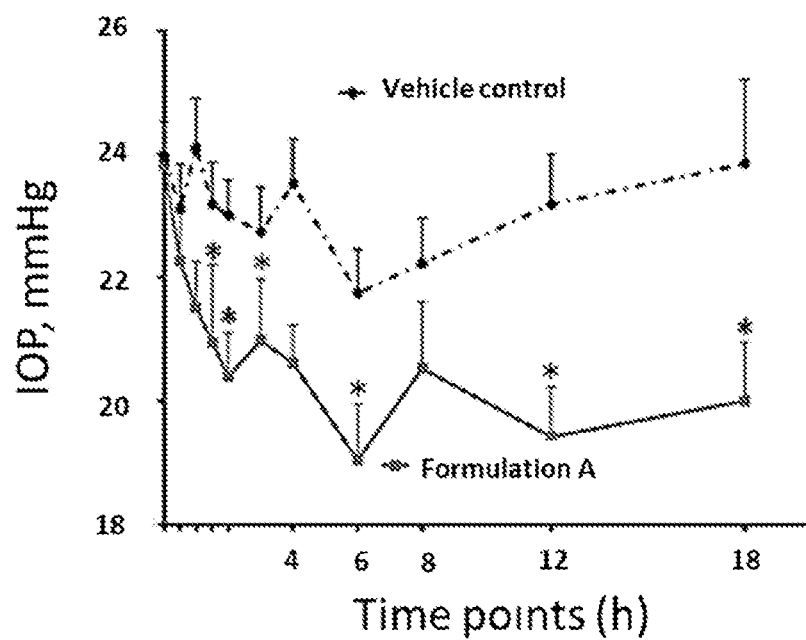

FIG. 2 presents the effect of an exemplary formulation of the invention, designated Formulation A (low-BKC), in reducing IOP in a steroid-induced ocular hypertension rat model, as determined by a controlled study.

Figure 3:
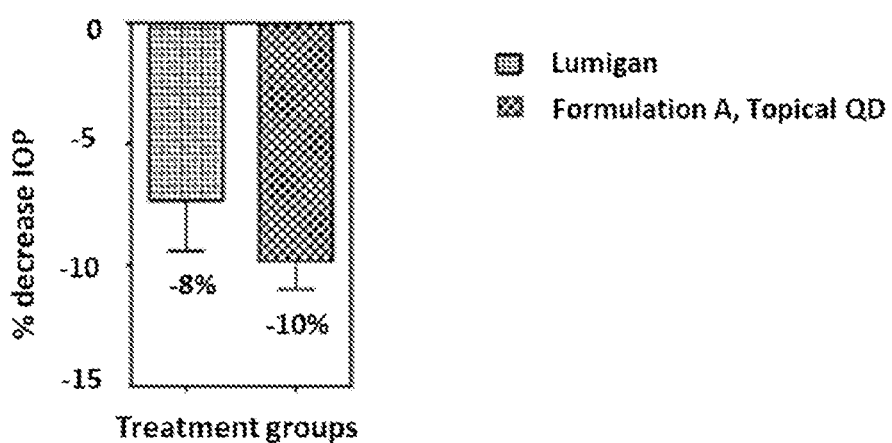

FIG. 3 presents the average percent decrease in IOP for LUMIGAN® 0.01% and Formulation A (low-BKC) compared to their respective control vehicles as determined by a controlled study.

DETAILED DESCRIPTION OF THE INVENTION

The invention herein, in aspects, is directed to ophthalmologically safe, low concentration-bimatoprost compositions, comprising low concentrations of benzalkonium chloride (BKC), yet which are surprisingly capable of reducing intraocular pressure in an amount statistically equivalent to that of LUMIGAN® 0.01%, without invoking the negative side effects known in the art related to bimatoprost and to BKC. The reduced concentration formulations of the invention described herein can, in aspects, provide statistically equivalent reductions in intraocular pressure as measured by appropriately conducted studies through the incorporation of, in certain embodiments, one or more secondary penetration enhancer compounds. In aspects, formulations of the present invention further comprise one or more tertiary penetration enhancer compounds. According to certain embodiments, providing sufficient penetration capabilities for low amounts of bimatoprost using low amounts of bimatoprost supplemented with at least one secondary penetration enhancer, provide for formulations capable of effectively reducing elevated intraocular pressure in patients suffering from the same.

In aspects of the invention, reference to LUMIGAN® 0.01%, e.g., in comparing characteristics of the formulations described herein thereto, is to LUMIGAN® 0.01% as presented in Table 1. In alternative aspects, reference to LUMIGAN® 0.01%, e.g., in comparing characteristics of the formulations described herein thereto, is to any LUMIGAN® 0.01% which has been or is, as of the time of this application, marketed in the United States.

According to certain embodiments, the invention herein describes ophthalmologically safe formulations comprising about 0.005% to about 0.02% of a bimatoprost compound; about 0.003-about 0.007% benzalkonium chloride, and an effective amount of at least one secondary penetration enhancer that detectably enhances penetration of the bimatoprost into a mammalian eye. In aspects, an effective amount of the composition results in a reduction of intraocular pressure in a mammalian eye that is at least statistically comparable to the same amount of a composition comprising the same amount of bimatoprost compound and at least about 200% more BKC. In certain embodiments, the invention is a method of producing such a formulation. In certain further embodiments, the invention is a method of reducing intraocular pressure in a mammalian eye using such a formulation.

Bimatoprost

As described in the background of the present application, bimatoprost ((Z)-7-[(1R, 2R, 3R, 5S)-3, 5-Dihydroxy-2-[(1E, 3S)-3-hydroxy-5-phenyl-1-pentenyl] cyclopentyl]-5-N-ethylheptenamide) is a prostamide and a synthetic analogue of prostaglandin $F_{2\alpha}$ ($PGF_{2\alpha}$), having a molecular weight of 415.58, a molecular formula of $C_{25}H_{37}NO_4$, and the following molecular structure:

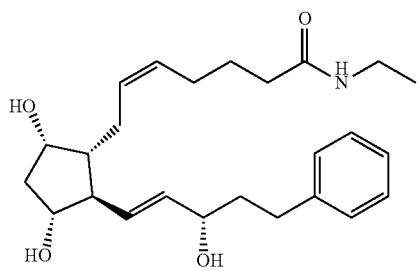 [SMILES: CCNC(=O)CCC/C=C\C[C@@H]1[C@@H](/C=C/[C@@H](O)CCc2ccccc2)[C@H](O)C[C@@H]1O]

In aspects, the invention provides compositions comprising a therapeutically effective amount of bimatoprost (an amount capable of inducing a statistically significant improvement in one or more conditions, such as reducing IOP, treating glaucoma, etc.). In aspects, as also previously described, bimatoprost works to lower intraocular pressure ("IOP") in patients with ocular hypertension (e.g., as often experienced by glaucoma patients) by increasing outflow of aqueous humor through both the trabecular meshwork and uveoscleral routes.

In aspects, formulations of the invention can comprise bimatoprost in any ophthalmologically acceptable form, such as for example bimatoprost in amorphous or crystalline forms (including polymorphic forms thereof); a pharmaceutically acceptable salt of bimatoprost (e.g., a tromethamine salt thereof); or any mixtures thereof suitable for ophthalmic use. Accordingly, the term "bimatoprost", as used herein, in aspects can be interpreted as referring to any bimatoprost compound; that is, bimatoprost or any related compound above, e.g., one or more of its pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs and pharmaceutically acceptable prodrugs thereof. In aspects "bimatoprost" can refer to any metabolite, analog, or a derivative of bimatoprost capable of exhibiting functional and physical responses that are significantly similar to that of bimatoprost, e.g., such functional and physical responses similar to those of prostaglandins and/or metabolites, analogs or derivatives of bimatoprost exhibiting prostaglandin receptor activity. In aspects "bimatoprost" refers to bimatoprost in hydrolyzed form. In aspects, "bimatoprost" refers to bimatoprost in free form or free acid form. In aspects, the bimatoprost of the formulation is limited to only one, two, or some larger combination of the various types of bimatoprost compounds described herein or their equivalents known in the art. In aspects, the bimatoprost component of a formulation is limited to one form of bimatoprost. In aspects, bimatoprost is the only active pharmaceutical ingredient in the formulation. In aspects, the bimatoprost component of formulations consists of, substantially consists of, or consists essentially of the same form of bimatoprost as in forms of LUMIGAN®, as marketed as of the date of this disclosure.

In aspects, formulation(s) of the invention can comprise any suitable amount of bimatoprost. In aspects, the amount of bimatoprost is set to a specific amount or range. In certain aspects, the formulations described herein can comprise between about 0.001-about 0.05% bimatoprost, such as between about 0.002-about 0.04%, between about 0.003-about 0.03%, or between about 0.004-about 0.02% bimatoprost, such as for example between about 0.005-about 0.02% bimatoprost, 0.0075-0.015% bimatoprost, or, e.g., between about 0.009-0.011% bimatoprost.

Benzalkonium Chloride (BKC)

As previously alluded to, penetration of bimatoprost into ocular tissue can be an important factor in the efficacy of ocular bimatoprost formulations. In aspects, benzalkonium chloride (abbreviated herein as BKC, though in other literature other abbreviations such as BAC, BAK, or BZK may be used), as previously described, can be present to serve as a penetration enhancer, preservative, solubilizer, or any combination thereof in the formulations of the present invention. Benzalkonium chlorides, also known as alkyl dimethyl benzyl ammonium chlorides (or ADBAC), alkyl dimethyl (phenylmethyl) chlorides, or ammonium alkyl dimethyl benzyl chlorides, are a class of quaternary ammonium compounds. These compounds comprise organic salts and cationic surfactants, most frequently used as mixtures of compounds having varying alkyl chain lengths, ranging from C8-C18. See, e.g., Merchel Piovesan Pereira B, Tagkopoulos I. Benzalkonium Chlorides: Uses, Regulatory Status, and Microbial Resistance. Appl Environ Microbiol. 2019; 85(13):e00377-19. Published 2019 Jun. 17. doi: 10.1128/AEM.00377-19. Typically, the BKC component of a formulation will exhibit detectable or significant antimicrobial (preservative) properties, can detectably or significantly aid in the solubilization of actives such as bimatoprost, and can detectably or significantly act as penetration enhancers improving the penetration of compounds into target tissues over the active alone. In aspects, any suitable BKC or combination thereof is used as a BKC component of a formulation of the invention. In certain aspects, BKCs comprising higher amounts of compounds having alkyl chain lengths ranging from C12-C14 that demonstrate higher antimicrobial/biocide activity are in the BKC component, primarily make up the BKC component, or make up substantially all or all of the BKC component. In aspects the BKC primarily comprises, substantially consists of, consists essentially of, or consists of benzyl ammonium chloride.

In aspects, benzalkonium chloride is present in the formulations of the invention in an amount equivalent to less than about 0.009% by weight, less than about 0.0085% by weight, less than about 0.008% by weight, such as less than about 0.0075% by weight, less than about 0.007% by weight, less than about 0.0065% by weight, less than about 0.006% by weight, or less than about 0.0055% by weight, as in for example less than about 0.005% by weight, such as less than about 0.0045% by weight, less than about 0.004% by weight, less than about 0.0035% by weight, less than about 0.003% by weight, less than about 0.0025% by weight, or even less, such as less than about 0.002% by weight, less than about 0.0015% by weight, or less than about 0.001% by weight. In aspects, formulations described herein comprise between about 0.002-about 0.009% by weight, between about 0.0025-about 0.008% by weight, between about 0.003-about 0.007% by weight, between about 0.004%-about 0.006% by weight, or for example between about 0.004%-about 0.005% by weight.

In certain facets, BKC is present in the formulations of the invention in an amount less than about 150 ppm, such as less than about 140 ppm, less than about 130 ppm, less than about 120 ppm, or less than about 110 ppm. In some aspects, BKC is present in the formulations in an amount less than approximately 100 ppm, such as less than approximately 95 ppm, less than approximately 90 ppm, less than approximately 85 ppm, less than approximately 80 ppm, or less than approximately 75 ppm, or even less, such as less than about 70, less than about 65, less than about 60, less than about 55, or less than about 50 ppm or even less.

In another general aspect, the ophthalmic formulations described herein comprise about 0.01% bimatoprost by weight and further comprise less than 100 ppm of benzalkonium chloride. Embodiments of this aspect include 95 ppm or less of benzalkonium chloride, 90 ppm or less of benzalkonium chloride, 85 ppm or less of benzalkonium chloride, 80 ppm or less of benzalkonium chloride, 75 ppm or less of benzalkonium chloride, 70 ppm or less of benzalkonium chloride, 65 ppm or less of benzalkonium chloride, 55 ppm or less of benzalkonium chloride, or individual integer values between 100 ppm and 50 ppm. In another aspect, the ophthalmic formulations described herein comprise about 0.01% bimatoprost by weight and less than 50 ppm of BKC, such as less than about 45 ppm, less than about 40 ppm, less than about 35 ppm, less than about 30 ppm, less than about 25 ppm, less than about 20 ppm, less than about 15 ppm, or less than about 10 ppm BKC, such as, e.g., between about 10-about 50 ppm BKC.

In some facets, presence of BKC in the formulation can improve upon the penetration of bimatoprost into ocular tissue by at least about 50%, at least about 60%, at least about 70%, at least about 80%, at least about 90%, or by at least 100% or more, such as at least about 110%, at least about 120%, at least about 130%, at least about 140%, at least about 150%, or even more, such as at least about 175%, at least about 200%, at least about 225%, at least about 250%, at least about 275%, at least about 300%, at least about 325%, at least about 350%, at least about 375%, at least about 400%, at least about 425%, or even as much as at least about 450% or more over that of a formulation of LUMIGAN® comprising 0.015% bimatoprost and 200 ppm of benzalkonium chloride (LUMIGAN® 0.01%).

Secondary Penetration Enhancers

In some aspects, the formulations described herein comprise one or more secondary penetration enhancers. In some respects, the secondary penetration enhancer can be any ophthalmologically suitable compound or mixture of compounds capable of exerting the effect of increasing the penetration of bimatoprost present in the formulation to an extent which results in an effective lowering of intraocular pressure. In aspects, the secondary penetration enhancer detectably or significantly enhances penetration of the bimatoprost into ocular tissue by at least about 10%, at least about 20%, at least about 30%, at least about 40%, at least about 50%, at least about 60%, at least about 70%, at least about 80%, at least about 90%, or by at least about 100%, such as at least approximately 120%, at least approximately 140%, at least approximately 160%, at least approximately 180%, or at least approximately 200% or even more, over similar formulations lacking a secondary penetration enhancer.

According to some embodiments, the benzalkonium chloride present in the formulation is present solely for preservative effect (e.g., only exhibits a significant effect in terms of preservative properties). In aspects, BKC is present in an amount less than 100 ppm. In aspects, the "secondary" penetration enhancer provides most, generally all, substantially all, or all the penetration enhancement of bimatoprost into ocular tissue.

In aspects, the secondary penetration enhancer can be present in the formulations of the invention in an amount of at least 0.05%, such as at least about 0.06%, at least about 0.07%, at least about 0.08%, at least about 0.09%, or at least about 0.1%. In aspects, a secondary penetration enhancer can be present in an amount of at least 0.1-5%, such as between about 0.12-about 4.5%, about 0.14%-about 4%, about 0.16%-about 3.5%, about 0.18%-about 3%, or about 0.2%-about 2.5%. In aspects, the concentration of secondary penetration enhancer in the formulations described herein is at least about 0.5%, at least about 0.6%, at least about 0.7%, at least about 0.8%, at least about 0.9%, or at least about 1%, such as between about 0.5-about 5%, between about 0.6-about 5%, between about 0.7-about 5%, between about 0.8-about 5%, between about 0.9-about 5%, or between about 1% and about 5%, such as between about 1% and about 4%, or for example between about 1% and about 3%, between about 1% and about 2%.

In certain facets, the secondary penetration enhancer can provide additional functionality to the formulation beyond the enhancement of bimatoprost into ocular tissue. In aspects, a secondary penetration enhancer can be characterized as a surfactant. In aspects, a secondary penetration enhancer can provide biocidal characteristics. In aspects, the secondary penetration enhancer aids in the preservation of the formulation, such that a suitable shelf life is maintained. In some facets, a secondary penetration enhancer can aid in maintaining the shelf life of a formulation of, e.g., at least about 1 week, at least about 2 weeks, at least about 1 month, at least about 8 weeks, at least about 2 months, at least about 3 months, at least about 4 months, at least about 6 months, at least about 8 months, at least about 10 months, or at least about 1 year when stored under appropriate storage conditions, in a cool, dry location at about room temperature (e.g., about 20-30° C., such as about 20-28 or 22-28° C., e.g., about 25° C., and between about 25-55% humidity, or any other set of conditions used for stability testing of an established regulatory agency, such as US FDA).

In certain respects, one or more secondary penetration enhancers can aid in solubilizing an active or an excipient. In certain aspects, one or more secondary penetration enhancers can support the solubilization of bimatoprost. In certain aspects, one or more secondary penetration enhancers can improve the solubilization of one or more excipients of the formulation such that a clear solution is maintained over extended periods of time, such as, e.g., at least 1 about month, at least about 2 months, at least about 4 months, at least about 6 months, at least about 8 months, or e.g., at least about 1 year.

In aspects, compounds suitable to serve as surfactants, bimatoprost penetration enhancers, and/or which may provide one or more additional functional activities to the formulation, such as, e.g., antimicrobial activity, include compounds which are ophthalmologically acceptable, suitable for topical application to the eye. In aspects, such compounds are non-ionic surfactants which can be safely utilized in concentrations ranging from 0.2-5%, e.g., between about 0.4-about 4.5%, between about 0.6-about 4%, between about 0.8-about 3.5%, or, e.g., between about 1% and about 3%.

In aspects, compounds suitable for use in the present invention for increasing the penetration of bimatoprost within ocular tissue, which may further provide additional functional activity (e.g., may provide surfactant activity, or, e.g., antimicrobial (e.g., preservative) activity) include but may not be limited to polyoxyethylene sorbitan fatty acid esters (e.g., polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80). In some aspects, characteristics of such a polyoxyethylene sorbitan fatty acid ester may be such that in specific concentrations the compound becomes unsuitable for ocular applications such as those described herein, as may be the case with, for example, polysorbate 20, as negative effects on ocular cells are possible. Hence in aspects, polysorbate 60, polysorbate 65, or polysorbate 80 may be more suitable for the formulations described herein.

According to certain embodiments, a secondary penetration enhancer can be characterized as a nonionic surfactant and emulsifier, clear in aqueous solution, non-irritating to ocular tissue, and capable of increasing the penetration of bimatoprost within ocular tissue, including any such compound modified in such a way that does not lead to a detectable or significant difference with respect to some, most, or generally all such characteristics with respect to an amount of polysorbate 80 that achieves a statistically similar level of penetration of the bimatoprost. In certain specific aspects, a secondary penetration enhancer can be a polyoxyethylene sorbitan fatty acid ester making up at least about 0.2%, at least about 0.5%, at least about 0.85%, or at least about 1% of the composition, such as between about 0.1-about 3% of the composition, such as between about 0.15-about 2.5%, or for example such as making up between about 0.2-2% of the formulation, e.g., between about 0.5%-about 1.5% of the formulation. In aspects, the polyoxyethylene sorbitan fatty acid ester is or consists essentially of polysorbate 80.

In aspects, additional compounds suitable for use in the present invention for increasing the penetration of bimatoprost within ocular tissue, which again may provide additional functional activity include quaternary ammonium compounds, such as, e.g., an ophthalmologically suitable quaternary ammonium salt. Quaternary ammonium compounds include ammonium salts in which organic radicals have been substituted for all four hydrogens of the original ammonium cation. Such compounds typically have a structure comprising a central nitrogen atom which is joined to four organic radicals and one acid radical. The organic radicals may be alkyl, aryl, or aralkyl, and the nitrogen can be part of a ring system. Examples of such compounds include Benzalkonium Chloride (e.g., CAS RN: 8001-54-5); Benzethonium Chloride CAS 121-54-0; Cetalkonium Chloride (e.g., CAS 122-18-9); Cetrimide (e.g., CAS 8044-71-1); Cetrimonium Bromide (e.g., CAS 57-09-0); Cetylpyridinium Chloride (e.g., CAS 123-03-5); and Stearalkonium Chloride (e.g., CAS 122-19-0), provided that typically the quaternary ammonium compound included in any formulation provided herein is of a nature and amount that is ophthalmologically safe and having the properties specified herein (e.g., in terms of bimatoprost penetration enhancement).

In aspects, a secondary penetration enhancer can be benzethonium chloride, benzyltrimethylammonium chloride (also known as Triton B or trimethylbenzylammonium hydroxide), or lauryl trimethyl ammonium chloride (also known as dodecyltrimethylammonium chloride). In some embodiments, the ophthalmic formulations of the invention lack any quaternary ammonium salt. In some aspects, formulations described herein comprise polyoxyl n castor oils (n=35-40) and polyoxyl hydrogenated castor oils, such as for example polyoxyl 35 castor oil (e.g., Cremophor EL), polyoxyl 40 castor oil (e.g., Marlowet 40, Emulgin RO 40), a polyoxyethylene hydrogenated castor oil (such as, e.g., polyoxyethylene hydrogenated castor oil 10/polyoxyl 10 hydrogenated castor oil, polyoxyethylene hydrogenated castor oil 40/polyoxyl 40 hydrogenated castor oil (Cremophor RH 40), polyoxyethylene hydrogenated castor oil 50/polyoxyl 50 hydrogenated castor oil, and polyoxyethylene hydrogenated castor oil 60/polyoxyl 60 hydrogenated castor oil (Cremophor RH 60)). In aspects, one suitable polyoxyl castor oil is polyoxyl-35-castor oil. In aspects, other compounds suitable as secondary penetration enhancers include tromethamine (tris), polyarginine, polyserine, or certain vegetable oils such as sesame seed oil or oils having similar compositions and functional characteristics suitable for ophthalmic use.

In certain facets, other suitable compounds for use as secondary penetration enhancers in the formulations described herein include but may not be limited to a polyoxyethylene polyoxypropylene glycol, e.g., a polyoxyethylene (160) polyoxypropylene (30) glycol (Pluronic F68), a polyoxyethylene (42) polyoxypropylene (67) glycol (Pluronic P123), a polyoxyethylene (54) polyoxypropylene (39) glycol (Pluronic P85); a polyoxyethylene (196) polyoxypropylene (67) glycol (Pluronic F127) and a polyoxyethylene (20) polyoxypropylene (20) glycol (Pluronic L-44); or a polyethylene glycol fatty acid ester, such as mono-lauric acid polyethylene glycol, monostearin acid ethylene glycol, monostearin acid polyethylene glycol, the mono-oleic acid polyethylene glycol, monostearin acid ethylene glycol, an ethylene glycol distearate, the distearic acid polyethylene glycol, and diiso stearic-acid polyethylene glycol. In aspects, a suitable compound is polyoxyl 40 stearate. In other aspects, tyloxapol is a suitable compound for use in the formulations described herein. In further aspects, poloxamers (block copolymers) of certain examples above, such as a polyoxyethylene-polyoxypropylene block copolymer (e.g., Pluronic F-68 from BASF) and polaxamines (copolymers of three long chains of ethylene oxide and a single chain of propylene oxide that are used as nonionic surfactants) are compounds suitable for use in the formulations herein.

In some facets, the secondary penetration enhancer can be an ophthalmologically suitable nonionic surfactant having an HLB value of at least about 14, at least about 14.5, at least about 15, at least about 15.5, at least about 16, at least about 16.5, or at least about 17, such as between about 14.5-about 17.5, between about 14.5-about 17.25, between about 14.5-about 17, or between about 14.5-about 16.75. In aspects, a secondary penetration enhancer has an HLB value of at least about 14 but no greater than about 17.75, no greater than about 17.5, no greater than about 17.25, no greater than about 17, or no greater than about 16.75.

In certain aspects, formulations described herein can further comprise one or more tertiary penetration enhancers. In aspects, such a tertiary penetration enhancer can further promote the penetration of bimatoprost into ocular tissue and is capable of detectably or significantly enhancing such penetration over that of the same formulation absent the tertiary penetration enhancer. In aspects, such a tertiary penetration enhancer can be any one or more of the penetration enhancers described above. In aspects, a tertiary penetration enhancer can be TPGS, tromethamine, polyarginine, polyserine, or certain vegetable oils such as sesame seed oil.

According to certain embodiments, the secondary penetration enhancer can comprise any combination of any two or more compounds described in the above paragraphs. In some embodiments, the secondary penetration enhancer can provide one or more additional functional benefits aside from penetration enhancement. In aspects, a secondary penetration enhancer can reduce a known side effect of bimatoprost, benzalkonium chloride, or both. Such effects are described elsewhere herein. In one aspect, a side effect can be dry eye, dry eye being a known side effect of high concentrations of BKC. In certain aspects, a secondary penetration enhancer can act as a demulcent and/or can reduce the effect of BKC in causing eye dryness. For example, according to one specific aspect, use of polysorbate 80 can detectably or significantly reduce the level of dry eye caused by the presence of benzalkonium chloride, as is discussed in detail elsewhere herein.

As non-limiting examples, in one aspect an ophthalmic formulation of the present invention can comprise about 0.01% bimatoprost by weight and about 50 ppm of benzalkonium chloride alone or in combination with one or more other penetration enhancers and solubilizers. In one example, a formulation can comprise about 0.01% bimatoprost by weight, 50 ppm of benzalkonium chloride alone or in combination with polysorbate 80, tocopherol polyethylene glycol succinate (TPGS), polyoxyl 35 castor oil, polyarginine, polyserine, tromethamine (tris), or sesame seed oil as a penetration enhancer and/or solubilizer. In an alternative example, an ophthalmic formulation can comprise about 0.01% bimatoprost by weight, about 50 ppm of benzalkonium chloride, and polysorbate 80, tocopherol polyethylene glycol succinate (TPGS), polyoxyl 35 castor oil, polyarginine, polyserine, tromethamine (tris), or sesame seed oil as penetration enhancer and/or solubilizer. In a further example, an ophthalmic formulation can comprise about 0.01% bimatoprost by weight, about 50 ppm of benzalkonium chloride, and tocopherol polyethylene glycol succinate (TPGS). In a final non-limiting example, an ophthalmic formulation can comprise about 0.01% bimatoprost by weight, about 50 ppm of BKC, and one or more of polysorbate 80, tromethamine (tris), polyarginine, polyserine, or certain vegetable oils such as sesame seed oil, benzethonium chloride, benzyltrimethylammonium chloride (also known as Triton B or trimethylbenzylammonium hydroxide), lauryl trimethyl ammonium chloride (also known as dodecyltrimethylammonium chloride), or polyoxyl-35-castor oil. Further non-limiting examples are provided in the Examples section of this disclosure. In aspects, any formulations described herein can be present with one or more excipients. Such excipients are discussed elsewhere herein.

According to some embodiments, the ophthalmological formulations described herein can be characterized by the compounds which are absent from the formulation. In aspects, ophthalmic formulation of the invention do not comprise any one or more of tocopherol polyethylene glycol succinate (TPGS), polyoxyethylene sorbitan monolaurate, polyoxyethylene sorbitan monostearate, a castor oil (e.g., a polyoxyl-35-castor oil), polyoxypropylene/polyoxyethylene block copolymers, polyoxypropylene/polyoxyethylene/ethylene diamine block copolymer, polyethylene glycol, benzododecinium bromide, polyethylene glycol hydroxystearate, polyoxyl-15-hydroxystearate, acetylated amino acids, polyethylene glycol 400, or polyethylene glycols individually (e.g., as single compounds and not as chains of larger compounds).

Other Excipients

In certain aspects, the ophthalmic formulations described herein can comprise one or more ophthalmologically suitable and pharmaceutically acceptable excipients. In aspects, the formulations comprise between about 0.005%-about 0.02% bimatoprost by weight, less than 100 ppm of BKC, and further comprise one or more such excipients.

According to some embodiments, excipients of the formulations described herein can be any ophthalmologically suitable and pharmaceutically acceptable excipients. In aspects, one or more excipients can be, but which may not be limited to, thickening agents or viscosity-enhancers, solubilizers, penetration enhancers, chelating agents, tonicity agents, buffers or pH-adjusting agents, preservatives and/or water.

According to some aspects, one or more thickening agents can be used in the ophthalmic formulations described herein to improve the form of the formulation for convenient administration and to improve contact with the eye and thereby improve bioavailability of, e.g., bimatoprost. Many such ophthalmologically suitable thickening agents are known in the art. Exemplary thickening agents include, but are not limited to, polymers containing hydrophilic groups such as monosaccharides and polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropylmethyl cellulose, povidone, polyvinyl alcohol, and polyethylene glycol. In certain aspects, formulations described herein lack any thickening (e.g., viscosity-enhancing) compounds or agents.

Osmolality of ophthalmic formulations can be important to efficacy and patient comfort. In aspects, the osmolality of the formulations described herein is suitable for ophthalmic application, such as for example between about 280-370 mOsmol/kg. In aspects, one or more tonicity agents may be included in the formulation to adjust the formulation such that it is within such a desired, suitable, or optimal isotonic range. In aspects, any ophthalmologically suitable and pharmaceutically acceptable tonicity agent can be used. In aspects, exemplary tonicity agents include, but are not limited to, glycerin, mannitol, sorbitol, sodium chloride, and other electrolytes. In certain aspects, one or more tonicity agents can be present in the formulation in an amount of between about 0.005%-about 0.85%, such as between about 0.006%-0.84%, between about 0.007%-about 0.83%, between about 0.008%-about 0.82%, between about 0.009%-about 0.81%, or for example between about 0.01%-about 0.8% by weight. In some aspects, sodium chloride is present in the formulations described herein. In aspects, the sodium chloride is present in an amount of between about 0.6-about 1% of the formulation, such as, e.g., between about 0.7-about 0.9% of the formulation, or, e.g., in an amount of about 0.8% of the formulation.

Chelating agents can be used in the ophthalmic compositions to enhance preservative effectiveness, e.g., by forming stable water-soluble complexes (chelates) with alkaline earth and heavy metal ions. In some aspects, formulations described herein can comprise one or more chelating agents. In aspects, such chelating agents can be any ophthalmologically suitable and pharmaceutically acceptable chelating agent, such as but which may not be limited to compounds capable of sequestering divalent or polyvalent metal cations and further remains effective at a pH of between about 6.5 and 8.0. In aspects, the chelating agent does not detectably or significantly impact the efficacy of any other component of the formulation. In aspects, exemplary chelating agents present in a formulation described herein can comprise but may not be limited to cromolyn, monomeric polyacids such as EDTA, cyclohexanediamine tetraacetic acid (CDTA), hydroxyethyl ethylenediamine triacetic acid (HEDTA), diethylenetriamine pentaacetic acid (DTPA), dimercaptopropane sulfonic acid (DMPS), dimercaptosuccnic acid (DMSA), aminotrimethylene phosphonic acid (ATPA), citric acid, any ophthalmologically acceptable salts thereof, and/or combinations of any two or more such compounds. In other aspects, a chelating agent can be a phosphate, such as, e.g., pyrophosphates, tripolyphosphates, and, hexametaphosphates; a chelating antibiotic such as chloroquine and tetracycline; a nitrogen-containing chelating agent containing two or more chelating nitrogen atoms within an imino group or in an aromatic ring (e.g., diimines, 2,2'-bipyridines, etc.); or for example a polyamine such as cyclam (1,4,7,11-tetraazacyclotetradecane), N—($C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomo-spermine (DEHOP), and deferoxamine (N'-[5-[[4-[[5-(acetylhydroxyamino)pentyl] amino]-1,4-dioxobutyl]hydroxy-amino]pentyl]-N'-(5-aminopentyl)-N-hydroxybutanediamide; also known as desferrioxamine B and DFO). In certain aspects, the formulations described herein comprise EDTA or an ophthalmologically suitable EDTA salt such as, e.g., diammonium EDTA, disodium EDTA, dipotassium EDTA, triammonium EDTA, trisodium EDTA, tripotassium EDTA, or calcium disodium EDTA.

According to embodiments, the formulations described herein can comprise one or more chelating agent(s) in an amount of between about 0.001-about 0.1%, such as between about 0.002-0.1%, between about 0.004-about 0.1%, between about 0.006-about 0.1%, between about 0.008-about 0.1%, or for example between about 0.01-about 0.1%. In certain embodiments, the concentration of one or more chelating agents can be much higher, such as for example between about 0.1-about 10 percent by weight. In embodiments wherein ethylenediaminetetraacetic acid (EDTA) is used, the chelating agent is preferably present in the formulation at a concentration of about 0.01% by weight. In certain aspects, citric acid monohydrate is present in the formulation and in facets such citric acid acts as a chelating agent. According to certain embodiments, citric acid can be present in the formulations described herein in an amount of approximately 0.001%-about 0.02%, such as for example between about 0.002-about 0.02%, between about 0.003-about 0.2%, between about 0.004-about 0.2%, between about 0.005-about 0.2%, such as between about 0.008-about 0.02%, or between about 0.01-about 0.018%, as in between about 0.01-about 0.016%, or between about 0.01-about 0.014%, such as about 0.014%.

In certain embodiments, the ophthalmic formulations described herein can comprise one or more buffers or pH-adjusting agents. In aspects, such agents can be used to adjust the pH to a desirable range, such as between about 6-about 8, such as between about 6.2-about 7.8, between about 6.4-about 7.6, between about 6.6-about 7.4, between about 6.8-about 7.2, or for example about 7.0-about 7.5, such as about 7.3. In some aspects, such a buffer may contribute the tonicity of the formulation, hence in some embodiments one or more buffers and one or more tonicity agents can combine to contribute to the osmolality of a formulation. In facets, any ophthalmologically suitable and pharmaceutically acceptable buffer may be used. In aspects, such buffers can include but may not be limited to dibasic sodium phosphate. In aspects sodium hydroxide and hydrochloric acid may be used during the production of the formulations herein to adjust pH to a target value, e.g., to a target value of approximately 7.0-7.5, such as about 7.3. In aspects, other buffers and other pH adjusters which are ophthalmologically suitable, pharmaceutically acceptable, and commonly used and known within the art can be present in the formulations herein. In specific aspects, the formulations described herein comprise dibasic sodium phosphate. In aspects, dibasic sodium phosphate is present in the formulation in a concentration of between about 0.05-0.35%, such as between about 0.06-about 0.32%, or between about 0.08-about 0.3%, between about 0.09-about 0.3%, or between about 0.1-about 0.3%. In some aspects, dibasic sodium phosphate is present in the formulation in a concentration of between about 0.2-about 0.3% by weight.

In some embodiments, the ophthalmic formulations described herein comprise one or more preservatives which detectably or significantly inhibit microbial growth. In aspects any ophthalmologically suitable and pharmaceutically acceptable preservative can be used. In aspects, exemplary preservatives can comprise but may not be limited to hydrogen peroxide; sorbic acid; biguanides; quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal and the like which may be known by those skilled in the art. In aspects, one or more preservatives may provide one or more other functional activities, such as for example detectably or significantly enhancing bimatoprost penetration. In certain aspects, the amount of preservative in the formulation is less than about 0.01%, such as less than about 0.009%, less than about 0.008%, less than about 0.007%, less than about 0.006%, or, e.g., less than about 0.005%. In aspects, benzalkonium chloride serves as the preservative in the formulations described herein, wherein the BKC is present in an amount between about 0.002%-about 0.008%, such as between about 0.004-about 0.006%, such as approximately 0.005%.

According to some embodiments, the formulations described herein are aqueous formulations comprising water (e.g., water for injection). In aspects, some, most, generally all, or all components of the formulation are fully dissolved such that a clear, aqueous solution is provided.

In some aspects, any one or more excipients described herein can be combined with any one or more additional excipients described herein in the formulations of the present invention. As a non-limiting example, an ophthalmic composition of the present invention can comprise about 0.01% bimatoprost by weight, a chelating agent, one or more tonicity agents, one or more buffers, one or more pH-adjusting agents, one or more preservatives, and water. In aspects, such a formulation can further comprise one or more secondary penetration enhancers. In aspects, such a formulation can further comprise one or more tertiary penetration enhancers. In aspects, such a formulation can further comprise a thickening agent or viscosity-enhancer.

Delivery Form

As discussed briefly elsewhere herein, in aspects the formulations of the present invention are in the form of an aqueous liquid solution for topical administration to a mammalian eye. In aspects the liquid is optically clear and suitable for administration to a mammalian eye without detrimentally affecting vision (e.g., without the formulation affecting vision of the recipient to an extent to which the recipient's vision prohibits the recipient from functioning at a level equivalent to that which the recipient was capable of functioning prior to application of the formulation). In alternative aspects, the formulations herein can be delivered as an emulsion, microemulsion, reverse emulsion, dispersion, suspension, or gel. In aspects, the formulations described herein are solutions which can be dropped as liquid drops to the eye(s) of the recipient.

According to aspects, the formulations of the present invention can be administered to the eye(s) of a recipient mammal from 1-6 times per day, such as about once per 24-hour period, twice per 24-hour period, three times per 24-hour period, 4 times per 24-hour period, 5 times per 24-hour period, or 6 times per 24-hour period. In aspects, formulations described herein are administered to a mammalian eye in need thereof approximately once per day. In aspects, a mammal may receive any such described administration regiment in one or both eyes. In aspects, administration to both eyes of the mammal can take place concurrently or at differing times.

Methods of Use

According to some aspects, the invention herein describes a method of reducing intraocular pressure in a mammal comprising administering an effective amount of any one or more ophthalmologically suitable compositions described herein, alone or in combination. In certain facets, the low concentration bimatoprost formulations (e.g., solutions) described herein offer advantages over existing, on-market bimatoprost formulations, in that such formulations are capable of reducing intraocular pressure in a mammal to an extent comparable to on market products without the side effects caused by higher concentrations of bimatoprost, higher concentrations of BKC, or both. The efficacy of such formulations is described further elsewhere herein.

In some facets, the invention herein describes a method of treating a mammal suffering from elevated intraocular pressure (IOP) by administering an effective amount of any one or more of the formulations described herein topically to the affected eye(s). In aspects, an effective amount is from 1-6 liquid drops per day, e.g., each drop having an average volume of about 20-about 75 µL, such as between about 25-about 70 µL, e.g., between about 30-about 65 µL, or between about 35-about 60 µL, such as having an average volume of about 35-about 55 µL, about 35-about 50 µL, about 35-about 50 µL, or for example between about 35-about 45 µL, such as for example on average about 40 µL. In some aspects, no more than about 450 µL of a formulation is administered to a single mammalian eye per day (e.g., per 24 hour period), such as no more than about 400 µL, no more than about 350 µL, no more than about 300 µL, no more than about 250 µL, no more than about 200 µL, no more than about 150 µL, no more than about 100 µL, or no more than about 50 µL, are administered to a single mammalian eye per 24-hour period.

In certain embodiments, the invention herein describes a method of evaluating whether a mammal or a population of mammals being administered an existing on market product can benefit from a formulation comprising reduced bimatoprost, reduced BKC, or both, such as through a reduction in one or more side effects of the existing on market product being experienced by the mammal. In aspects of such a method, the mammal can be administered a formulation described herein for a period of 1 or more days, e.g., 2 or more days, 3 or more days, 4 or more days, 5 or more days, 6 or more days, or for example at least about 7 days, such as about 1 week or about 2 weeks or more, and the side effects of the administered formulation compared to that (e.g., any) caused by the on-market product. In aspects such a method can be conducted through an appropriately powered and conducted clinical trial and/or alternatively such a method can be conducted on an individual basis as monitored by a prescribing medical professional.

Methods of Production

According to certain aspects the invention described herein is a method of producing any one or more of the ophthalmic formulations described in this disclosure.

In certain facets, the formulations described herein are aqueous solutions having, as a base, a reduced oxygen content. In aspects, the formulations described herein are produced by a method which can be described as having first and second parts. In aspects, part I of the method comprises first reducing the oxygen level of water for injection (WFI). In aspects, one or more penetration enhancers, surfactants, preservatives, or any combination thereof, wherein in certain aspects a single component can be described as having one or more of such characteristics, can be dissolved in the oxygen-reduced water for injection. In certain aspects, once dissolved, a penetration enhancer, preservative, or compound(s) having both characteristics can be added to the solution. According to some embodiments, the solution can then be monitored until the oxygen level drops below a pre-established threshold. In facets, once the oxygen level has dropped below the pre-established threshold, bimatoprost can be added and the solution can be stirred until the bimatoprost is completely dissolved. In aspects, separate and apart from the steps described above, as part II of the method, in a separate container an amount of oxygen-reduced WFI is established, to which is added one or more tonicity agents, one or more buffers, and one or more chelating agents. In some aspects, each component is added one at a time. In certain facets, each component is allowed to completely dissolve prior to the addition of the next component (e.g., the previous ingredient is in solution prior to the addition of the next one). According to embodiments, after such ingredients are completely dissolved, the pH of the solution can be established using a pH adjusting agent. In some aspects, once a suitable pH is established, the contents of a first part (part I) of the method can be transferred to and mixed with the contents of a second part (part II) of the method. In aspects the two components are sufficiently mixed so as to form a uniform solution. In aspects, the uniform solution is then adjusted to a final volume using WFI. The final solution can, in aspects, then be sterilized and filled into appropriate packaging.

According to some aspects, part I comprises using approximately 5-15%, such as about 6%-about 14%, about 7%-about 13%, about 8%-about 12%, about 9%-about 11%, or for example about 10% of the total WFI to be used in producing the formulation, such a volume heated and purged using nitrogen to reduce the amount of oxygen in the WFI to establish an oxygen-reduced WFI for use in part I of the method. In aspects, once purged, the oxygen-reduced WFI is cooled before the method continues. In aspects, the method continues once the WFI is cooled and the oxygen level is below, e.g., about 5 ppm, below about 4 ppm, below about 3 ppm, or below about 2 ppm, such as below about 1 ppm. In aspects, in part I of the method, bimatoprost is not added until again the oxygen level drops below about 5 ppm, below about 4 ppm, below about 3 ppm, below about 2 ppm, or below about 1 ppm. According to some further aspects, part II comprises initially using approximately 40-80%, such as about 42%-about 79%, about 44%-about 78%, about 46%-about 77%, about 48-about 76%, or for example about 50% or about 75% of the total WFI to be used in producing the formulation, such a volume heated and purged using nitrogen to reduce the amount of oxygen in the WFI to be used in the initial steps of part II of the method. In aspects, once purged, the oxygen-reduced WFI is cooled before the method continues. In aspects, the method continues once the WFI is cooled and the oxygen level is below, e.g., about 5 ppm, below about 4 ppm, below about 3 ppm, e.g., below about 2 ppm or 1 ppm.

According to certain aspects, the solution is sterilized prior to final packaging. In some facets, the invention describes a method of producing (e.g., a method of preparing) a formulation described herein wherein the method comprises a process for sterilizing the compositions in order to reduce the amount(s) of related compounds and impurities associated with the ophthalmic compositions which may be generated during storage. This is discussed further elsewhere herein. In aspects, the solution can be sterilized by any method suitable for the sterilization of a liquid which does not significantly impact the concentration or efficacy of any ingredient of the formulation. Exemplary sterilization methods include but may not be limited to heat sterilization gaseous sterilization, filtration sterilization, or radiation sterilization. In specific aspects, the formulations described herein are sterilized by filtration, with the produced formulations filtered through a sterilizing grade filter, such as for example a filter having a pore size of no greater than 0.22 µL.

In one general aspect, the invention disclosed herein provides a process for the preparation of an ophthalmic formulation comprising from about 0.005% to about 0.02% bimatoprost by weight, and one or more pharmaceutically acceptable excipients, wherein the formulation comprises less than about 100 ppm of benzalkonium chloride. In another general aspect, the invention provides a process for the preparation of an ophthalmic composition comprising from about 0.005% to about 0.02% bimatoprost by weight, about 50 ppm of benzalkonium chloride alone or in combination with one or more other penetration enhancers and/or solubilizers. In one aspect, such a penetration enhancer is polysorbate 80 in a concentration of about 1%. In another aspect, the invention provides a process for the preparation of an ophthalmic composition comprising from about 0.005% to about 0.02% bimatoprost by weight, about 50 ppm of benzalkonium chloride alone or in combination with polysorbate 80, tocopherol polyethylene glycol succinate (TPGS), polyoxyl 35 castor oil, polyarginine, polyserine, tromethamine (tris), sesame seed oil or any combination thereof as a penetration enhancer and/or solubilizer. In one further aspect, the invention herein provides a process for the preparation of an ophthalmic composition comprising from about 0.005% to about 0.02% bimatoprost by weight, about 50 ppm of benzalkonium chloride alone or in combination with polysorbate 80, tocopherol polyethylene glycol succinate (TPGS), polyoxyl 35 castor oil, polyarginine, polyserine, tromethamine (tris), sesame seed oil, or any combination thereof as a penetration enhancer and/or solubilizer, and one or more pharmaceutically acceptable excipients.

Examples of the production of multiple formulations using this method are provided in the Examples section of this disclosure.

Effects/Efficacy

The low (e.g., reduced) concentration bimatoprost formulations (e.g., solutions) described herein, comprising a low (e.g., reduced) concentration of BKC can, in aspects, provide advantages compared to or over known or existing on-market products such as LUMIGAN® 0.01% or LUMIGAN® 0.03%. In certain embodiments, the formulations described herein are detectably or significantly safer (e.g., having a reduced concentration of both bimatoprost and benzalkonium chloride) or detectably or significantly more tolerable (having a reduced risk of side effects due to bimatoprost and benzalkonium due to such compounds being present at lower concentrations) than currently available on-market bimatoprost formulations such as LUMIGAN® 0.01%. In some aspects, the formulations described herein are available to a broader population of patients than that of LUMIGAN® 0.01% or LUMIGAN® 0.03%, such as for example formulations of the present invention being capable of being administered to a significantly greater amount of human patients wearing soft contact lenses without significant absorption by the lens material, or further, by being tolerable by those having a particular sensitivity to higher levels of bimatoprost and/or BKC. In certain aspects, the formulations described herein provide such detectably or significantly greater safety, tolerability, and patient compliance benefits while maintaining or exceeding the IOP-lowering effects of compositions having higher bimatoprost and higher benzalkonium chloride concentrations.

In certain embodiments, patient compliance is at least about 2% higher, at least about 4% higher, at least about 6% higher, at least about 8% higher, at least about 10% higher, at least about 12% higher, at least about 14% higher or more, such as at least approximately 16% higher, at least approximately 18% higher, at least approximately 20% higher or even more than that of LUMIGAN® 0.01% or other bimatoprost formulations (e.g., as determined by comparison of compliance in groups of test patients, such as in a sufficiently powered study/studies of users of the respective products). In aspects this is at least in part due to a detectable or significant reduction in side effects, as measured by patient reporting, patient survey, or an appropriately conducted and powered clinical study. In some aspects, mammals, such as human patients, maintain use of the formulations described herein for periods which are at least 5%, at least 10%, at least 15%, or even at least 20% or more longer than such periods of use of other products comprising higher concentration of bimatoprost, a higher concentration of benzalkonium chloride, lacking polysorbate 80, or comprising different secondary bimatoprost penetration enhancer(s) but providing statistically comparable efficacy related to reduction of IOP, or any or all thereof. In aspects, recipients of formulations described herein can maintain use for periods of about 1 week, about 1 month, about 3 months, about 6 months, about 1 year, about 2 years, about 3 years, about 5 years, about 10 years, or for about 15 or 20 years or more without significant adverse effects causing a discontinuation of use.

According to some aspects, the ophthalmic compositions described herein exhibit at least substantially equivalent or greater bioavailability or penetration of bimatoprost in ocular tissue than that of on-market products such as LUMIGAN® 0.01%. In certain aspects, such effects are observed while concurrently causing fewer adverse events than the bimatoprost composition with higher amounts, e.g., up to 200% more, benzalkonium chloride. In certain facets, formulations described herein are capable of reducing the intraocular pressure in a treated mammalian eye by an amount that is at least statistically comparable to the same amount of a composition comprising the same amount of bimatoprost compound and at least 200% more benzalkonium chloride.

According to certain embodiments, the invention describes formulations for use in treating elevated intraocular pressure in mammalian eye(s) and, further, describes methods of using such formulations in the treatment of such conditions. According to some aspects, use of formulations described herein results in a detectably or significantly greater reduction in intraocular pressure over that obtained by use of LUMIGAN® 0.01% as measured about 2, about 4, about 6, about 8, about 10, about 12, about 14, about 16, about 18, about 20, about 22, or about 24 hours, or any combination thereof, after administration. In some aspects, use of formulations described herein results in a detectably or significantly greater reduction in intraocular pressure over that obtained by use of a control vehicle (e.g., the formulation minus the active) as measured about 2, about 4, about 6, about 8, about 10, about 12, about 14, about 16, about 18, about 20, about 22, or about 24 hours, or any combination thereof, after administration.

In certain aspects, use of the formulations described herein results in a reduction in intraocular pressure in a mammalian eye suffering from an increase in intraocular pressure of at least about 20%, at least about 25%, at least about 30%, at least about 35%, at least about 40%, at least about 45%, or for example at least about 50% above normal by at least an average of about 1% more, such as at least about 1% or at least about 2% more than use of LUMIGAN® 0.01% when measured in a statistically significant population of mammals in an appropriately powered and administered study.

In particular facets, use of the formulations described herein results in a reduction in intraocular pressure in a mammalian eye suffering from increased intraocular pressure of at least about 20%, at least about 25%, at least about 30%, at least about 35%, at least about 40%, at least about 45%, or for example at least about 50% above normal by at least about 5%, at least about 6%, at least about 7%, at least about 8%, at least about 9%, or at least about 10% when measured in a statistically significant population of mammals in an appropriately powered and administered study.

The formulations described herein, as previously described, can reduce the adverse effects of similar on market bimatoprost products such as, for example LUMIGAN® 0.01%, which comprise higher amounts of BKC. According to certain embodiments, formulations described herein can reduce hyperemia, e.g., conjunctival hyperemia (eye redness), by at least about 1%, at least about 2%, at least about 3%, at least about 4%, or at least about 5% or more over products comprising a higher concentration of bimatoprost, a higher concentration of benzalkonium chloride, lacking polysorbate 80, or comprising different secondary bimatoprost penetration enhancer(s) but providing statistically comparable efficacy related to reduction of IOP, or any or all thereof.

In some aspects, formulations described herein can reduce tear film instability, loss of goblet cells, conjunctival squamous metaplasia and apoptosis, disruption of the corneal epithelium barrier, and damage to deeper ocular tissues by at least about 1%, at least about 2%, at least about 3%, at least about 4%, or at least about 5% or more over products comprising a higher concentration of bimatoprost, a higher concentration of benzalkonium chloride, lacking polysorbate 80, or comprising different secondary bimatoprost penetration enhancer(s) but providing statistically comparable efficacy related to reduction of IOP, or any or all thereof.

In further embodiments, formulations described herein can reduce visual disturbance, ocular burning, foreign body sensation, eye pain, blepharitis, cataract, superficial punctate keratitis, eyelid erythema, general ocular irritation, eye discharge, tearing, photophobia, allergic conjunctivitis, asthenopia, conjunctival edema, conjunctival hemorrhage, intraocular inflammation, or any combination thereof by at least about 1%, at least about 2%, at least about 3%, at least about 4%, or at least about 5% or more over products comprising a higher concentration of bimatoprost, a higher concentration of benzalkonium chloride, lacking polysorbate 80, or comprising different secondary bimatoprost penetration enhancer(s) but providing statistically comparable efficacy related to reduction of IOP, or any or all thereof.

According to one aspect, use of a secondary penetration enhancer, an excipient, or a combination thereof, can detectably or significantly reduce the level of eye dryness caused by (a) formulations comprising higher amounts of benzalkonium chloride, (b) formulations described herein, e.g., comprising about 50 ppm BKC absent a secondary penetration enhancer and/or excipient, or both (a) and (b). In certain facets, the level of eye dryness is at least about 1% lower, at least about 2% lower, at least about 3% lower, at least about 4% lower, at least about 5% lower, or even more, such as at least about 6% lower, at least about 8% lower, at least about 10% lower, or even more, than such formulations. In specific aspects, use of polysorbate 80 in the formulations described herein can reduce the level of eye dryness caused by formulations comprising higher amounts of BKC or caused by formulations described herein absent polysorbate 80, by such amounts.

According to particular facets, at least about 1%, such as at least about 2%, at least about 3%, at least about 4%, at least about 5%, at least about 6%, at least about 7%, at least about 8%, at least about 9%, or at least about 10% or more fewer patients experience hypersensitivity reactions than similar formulations with a higher concentration of bimatoprost, a higher concentration of BKC, or other formulations comprising different secondary penetration agents with statistically comparable IOP reduction capability.

As previously stated, the formulations of the present invention can be available to soft contact lens wearers due to the reduced concentration of bimatoprost. In aspects, at least about 1%, such as at least about 2%, at least about 3%, at least about 4%, at least about 5%, at least about 6%, at least about 7%, at least about 8%, at least about 9%, or at least about 10% less bimatoprost is absorbed by soft contact lenses from formulations described herein as compared to formulations comprising higher amounts of bimatoprost, such as, e.g., LUMIGAN® 0.01% or LUMIGAN® 0.03%. In aspects, less than about 10%, such as less than about 9%, less than about 8%, less than about 7%, less than about 6%, less than about 5%, less than about 4%, less than about 3%, less than about 2%, or less than about 1% of soft contact lens wearers discontinue use of the formulations described herein due to absorption complications, as measured by patient reporting, patient survey(s), or by an appropriately powered and conducted clinical study.

Stability Characteristics

The formulations of the present invention are capable of maintaining stability for a sufficient amount of time to provide for an adequate shelf life of the product. In certain aspects, formulations described herein are capable of maintaining the concentration of bimatoprost within about 10%, such as within about 9%, within about 8%, within about 7%, within about 6%, or even within about 5% of that of the initial concentration of bimatoprost when stored up to at least about 1 month, at least about 2 months, at least about 3 months or more at 40° C. and 25% relative humidity, when stored at 25° C. and 40% relative humidity, or both, when measured in an appropriately controlled and conducted stability study. In aspects, the formulations described herein can comprise approximately 0.01% bimatoprost by weight, less than about 100 ppm of BKC, and is characterizable as being capable of retaining at least about 90% w/w, such as at least about 91%, at least about 92%, at least about 93%, at least about 94%, at least about 95%, at least about 96%, at least about 97%, at least about 98%, at least about 99%, or even more of the potency of bimatoprost compound when stored at 25° C. and 40% relative humidity or at 40° C. and 25% relative humidity for 3 months.

In some embodiments, formulations described herein are capable of maintaining the concentration of the bimatoprost impurity 15 (R) bimatoprost below about 0.3%, such as below about 0.25%, below about 0.2%, below about 0.15%, or even below about 0.1% when stored for at least up to 3 months at 40 degrees Celsius and 25% relative humidity, when stored up to at least about 1 month, at least about 2 months, at least about 3 months or more at 40° C. and 25% relative humidity, when stored at 25° C. and 40% relative humidity, or both, when measured in an appropriately controlled and conducted stability study.

In some embodiments, formulations described herein are capable of maintaining the concentration of the bimatoprost impurity 15 keto bimatoprost below about 0.7%, such as below about 0.65%, below about 0.6%, below about 0.55%, below about 0.5%, below about 0.45%, below about 0.4%, below about 0.35%, below about 0.3%, below about 0.25%, below about 0.2%, below about 0.15%, or even below 0.1% when stored up to at least about 1 month, at least about 2 months, at least about 3 months or more at 40° C. and 25% relative humidity, when stored at 25° C. and 40% relative humidity, or both, when measured in an appropriately controlled and conducted stability study.

In one facet, formulations described herein are capable of maintaining the concentration of the bimatoprost impurity bimatoprost acid below about 0.5%, such as below about 0.45%, below about 0.4%, below about 0.35%, below about 0.3%, below about 0.25%, below about 0.2%, below about 0.15%, or even below about 0.1% when stored up to at least about 1 month, at least about 2 months, at least about 3 months or more at 40° C. and 25% relative humidity, when stored at 25° C. and 40% relative humidity, or both, when measured in an appropriately controlled and conducted stability study.

In a further aspect, formulations described herein are capable of maintaining the concentration of bimatoprost impurities having a relative retention time as measured by HPLC of 0.28 below about 0.3%, such as below about 0.25%, below about 0.2%, below about 0.15%, or even below about 0.1% when stored for at least up to 3 months at 40 degrees Celsius and 25% relative humidity, when stored for up to at least about 1 month, at least about 2 months, at least about 3 months or more at 40° C. and 25% relative humidity, when stored at 25° C. and 40% relative humidity, or both, when measured in an appropriately controlled and conducted stability study.

Generation of New Formulations: Methods of Production and Screening

In certain embodiments, new formulations comprising amounts of bimatoprost and other excipient(s) described herein, such as formulations comprising less than 0.01% bimatoprost and less than 100 ppm benzalkonium chloride, can be produced through screening various product candidates for efficacy in causing one or more of the physiological, physiochemical, or clinical/preclinical effect(s) described herein, such as reducing intraocular pressure (e.g., in treating glaucoma) in a suitable animal model, human patient population, or both. In certain aspects, formulations can be produced using any one or more secondary penetration enhancers, tertiary penetration enhancers, and/or excipients described herein or their functional equivalents known in the art (e.g., compounds having characteristics suitable for the formulations described herein, such as being, e.g., ophthalmologically suitable and pharmaceutically acceptable), and screened using in vitro or in vivo models to assess efficacy in reduction of intraocular pressure. In aspects, one or more proposed formulations can be compared against existing products, e.g., against LUMIGAN® 0.01%. In aspects, proposed formulations can vary in amounts of one or more components, ratios of one or more components, in pH, in viscosity, in treatment volume, or other such formulation-related aspects, or in, e.g., methods of production. In certain facets, methods of production can be screened concurrently with and/or separately from new formulations. In some embodiments, modifications in production steps such as, e.g., the temperature to which one or more components of the formulation are heated, the order in which one or more components of the formulation are added, the amount or method of stirring, the timing of one or more steps of the manufacturing process, the sterilization method, the filling (e.g., of final product bottle) process, the product bottle material, or any element of a step in a method of production can be modified and screened. In certain embodiments, methods of screening formulations or methods of production can result in formulations with improved efficacy, improved (e.g., lower) cost, longer shelf life and/or reduced impurities over time (e.g., improved stability), reduced side effects, or other such improvements over other formulations such as on-market products or those described herein.

It should be understood that the above description and Examples provided below are intended to be illustrative and not restrictive. Many embodiments will be apparent to those of skill in the art upon reading the above description and considering the provided Examples. The scope of the invention should, therefore, be determined with reference to the claims, along with the full scope of equivalents to which such claims are entitled. The disclosures of all articles and references, including patents, patent applications and publications, are incorporated herein by reference in their entirety and for all applicable purposes.

EXAMPLES

The following ophthalmologically suitable bimatoprost formulations were generated and evaluated for stability and effects on intraocular pressure (IOP) in a rat model. The purpose of stability and IOP studies was to demonstrate that formulations having the characteristics of formulations described herein can possess comparable stability and IOP-lowering results to the well-established LUMIGAN® 0.01% on-market ophthalmic product. Specifically, Formulation A (low-BKC, +polysorbate 80) is a formulation comprising the same amount of bimatoprost as LUMIGAN® 0.01% (0.10 mg/mL) but comprises only 25% of the amount of benzalkonium chloride (BKC) as LUMIGAN® 0.01%. Further, Formulation A comprises polysorbate 80 as a penetrant.

TABLE 1

Experimental formulations.

| INGREDIENTS | LUMIGAN® 0.01% FORMULATION | FORMULATION A (LOW-BKC) |
|---|---|---|
| Bimatoprost | 0.10 mg/mL | 0.10 mg/mL |
| Benzalkonium chloride NF | 0.2 mg/mL | 0.05 mg/mL |
| Sodium chloride USP | 8.30 mg/mL | 8.00 mg/mL |
| Dibasic sodium phosphate USP (Heptahydrate) | 2.68 mg/mL | 2.68 mg/mL |
| Citric acid USP monohydrate | 0.14 mg/mL | 0.14 mg/mL |
| Polysorbate 80 NF | — | 10 mg/mL |
| Sodium hydroxide NF | QS to adjust pH to 7.3 | QS to adjust pH to 7.3 |
| Hydrochloric acid | QS to adjust pH to 7.3 | QS to adjust pH to 7.3 |
| Water for injection USP | QS to 1 mL | QS to 1 mL |

Example 1

Accelerated stability testing was performed on both of the above-described formulations over the course of a 3-month period.

Samples were tested at time zero ("Initial") for content of: bimatoprost (%), benzalkonium chloride (%), 15 ® bimatoprost (%), 15 keto bimatoprost (%), bimatoprost acid (%), specified unidentified impurity at RRT 0.28(%), and any unspecified impurity (%). Total impurity (%) was calculated.

After testing at time zero, sample aliquots were stored at 40 degrees Celsius and 25% relative humidity and at 25 degrees Celsius and 40% relative humidity. Samples stored at 40° C./25% RH were tested at time periods of 1 month, 2 months, and 3 months. At 3 months after initiation, samples stored at 25° C./40% RH were also tested. The test parameters, stability specification, and all results are summarized in Table 2 (LUMIGAN® 0.01%) and Table 3 (Formulation A, Low-BKC) below. Table 4 provides a simplified summary of results.

TABLE 2

LUMIGAN® 0.01% Stability Data.

| Test Parameters | Specification | Initial | 40° C./25% RH | | | 25° C./40% RH |
| | | | 1M | 2M | 3M | 3M |
|---|---|---|---|---|---|---|
| Assay of bimatoprost (%) | 90.0-110.0% | 99.1 | 102.4 | 102.4 | 97.8 | 97.1 |
| Assay of benzalkonium chloride (%) | 90.0-110.0% | 93.7 | 91.9 | 94.8 | 94.2 | 93.4 |
| 15 (R) bimatoprost (%) | NMT 0.3% | 0.107 | 0.86 | 0.097 | ND | ND |
| 15 keto bimatoprost (%) | NMT 0.7% | 0.068 | 0.197 | 0.227 | 0.242 | 0.173 |
| Bimatoprost acid (%) | NMT 0.5% | ND | ND | 0.305 | ND | ND |
| Specified unidentified impurity at RRT 0.28 (%) | NMT 0.3% | ND | 0.100 | 0.123 | ND | ND |
| Any unspecified impurity (%) | NMT 0.3% | ND | 0.049 (RRT 0.97) | 0.052 (RRT 0.68) | 0.087 (RRT 0.952) | 0.086 (0.952) |

TABLE 2-continued

LUMIGAN® 0.01% Stability Data.

| Test Parameters | Specification | Initial | 40° C./ 25% RH | | | 25° C./ 40% RH |
|---|---|---|---|---|---|---|
| | | | 1M | 2M | 3M | 3M |
| Total impurity (%) | NMT 1.5% | 0.175 | 0.432 | 0.949 | 0.329 | 0.259 |
| pH | 6.8-7.8 | 7.02 | 7.18 | 7.10 | 7.08 | 6.88 |

(RRT = relative retention time; M = months; RH = relative humidity)

TABLE 3

Formulation A (Low-BKC) Stability Data.

| Test Parameters | Specification | Initial | 40° C./ 25% RH | | | 25° C./ 40% RH |
|---|---|---|---|---|---|---|
| | | | 1M | 2M | 3M | 3M |
| Assay of bimatoprost (%) | 90.0-110.0% | 97.4 | 97.0 | 98.9 | 97.9 | 96.8 |
| Assay of benzalkonium chloride (%) | 90.0-110.0% | 96.5 | | 98.1 | — | — |
| 15 (R) bimatoprost (%) | NMT 0.3% | 0.116 | 0.072 | 0.082 | ND | ND |
| 15 keto bimatoprost (%) | NMT 0.7% | 0.071 | 0.186 | 0.324 | 0.506 | 0.129 |
| Bimatoprost acid (%) | NMT 0.5% | ND | 0.130 | ND | ND | ND |
| Specified unidentified impurity at RRT 0.28 (%) | NMT 0.3% | ND | 0.065 | 0.148 | ND | ND |
| Any unspecified impurity (%) | NMT 0.3% | 0.041 (RRT 0.409) | ND | 0.099 (RRT 0.68) | 0.077 (RRT 0.95) | 0.108 (RRT 0.952) |
| Total impurity (%) | NMT 1.5% | 0.228 | 0.454 | 0.798 | 0.708 | 0.237 |
| pH | 6.8-7.8 | 7.26 | 7.06 | 7.33 | 7.10 | 7.18 |

(RRT = relative retention time; M = months; RH = relative humidity)

TABLE 4

Summary of stability data for Formulation A (low-BKC) and LUMIGAN® 0.01%.

| Formulation | Type of formulation | Assay of Bimatoprost (avg) |
|---|---|---|
| Formulation A (low-BKC) | 0.05 mg/mL BKC (50 ppm BKC) | 97.6% |
| LUMIGAN® 0.01% | 0.2 mg/mL BKC | 100.6% |

The results of these studies, presented in the Tables above, indicate that both LUMIGAN® 0.01% and Formulation A (low-BKC/+polysorbate 80) meet suitable/desirable purity specifications for pharmaceutical application. Average bimatoprost content (%) at 3 months (averaging results collected at both conditions) was 100.6% for LUMIGAN® 0.01% and 97.6% for Formulation A (low-BKC), indicating that the low-BKC formulation is capable of maintaining suitable stability while only comprising only 25% of the amount of BKC in the comparator (LUMIGAN® 0.01%) formulation and comprising a penetration-enhancing amount of a second penetration enhancer (here, polysorbate 80).

Example 2

The same formulations described above and used in the stability studies described in Example 1 were used in efficacy of topical administration of test formulations in steroid-induced intraocular pressure in a rat model.

Study Design

Male Sprague Dawley rats at approximately 14 weeks of age, after being clinically examined for good health and found suitable, were appropriately acclimated and used in this study. The study was conducted under controlled conditions and according to standard experimental animal care guidelines, regulations, and practice.

Rats were housed in a single, environment-controlled room at 20-23° C. and a relative humidity of 30-70% during the experimental period. The photoperiod was 12 hours light, 12 hours darkness. Adequate fresh air supply of 12-15 air changes/hour was maintained in the experimental room. Maximum and minimum temperatures and relative humidity in the experimental room was monitored and recorded once daily. Animals were housed 2 per cage in standard animal cages with facilities for pelleted, standard rodent diet food, and filtered, purified drinking water, which were provided ad libitum. Animals were acclimatized for 5 days after a quarantine period in a study room.

Post-acclimatization, the phenotype development phase was initiated. A topical ophthalmic dexamethasone formulation application was initiated, applying dexamethasone solutions to both the left and right eye of all rats to induce an increase in intraocular pressure (IOP). Use of a rat model for ocular pressure (e.g., in glaucoma research) is an accepted animal model in the art (see, for example the review article by Evangelho, et. al., "Experimental Models of Glaucoma: a Powerful Translational Tool for the Future Development of New Therapies for Glaucoma in Humans—A Review of the Literature", in *Medicina*, published 17 Jun. 2019.)

Two concentrations of dexamethasone formulation (0.1% and 0.3%) were evaluated in this phenotype development phase, with 50 rats in each dexamethasone concentration group. 30 µL of dexamethasone formulation was applied to each eye of all rats four times per day for 4 weeks. Three animals were maintained as a placebo group, wherein no corticosteroid was applied into the eyes of these animals. Saline was applied into the eyes of the placebo rats.

IOP was measured using a tonometer according to standard operating procedures consistently on a weekly basis for 4 weeks, starting at the day of first corticosteroid application.

At the end of week 4, 0.1% dexamethasone treated animals showed consistent IOP phenotype development in both eyes compared to 0.3% dexamethasone application and hence animals in the 0.1% dexamethasone group were selected for formulation evaluation. Animals from the 0.5% dexamethasone group did not participate in the formulation testing phase of the study.

IOP was measured and animals were segregated based upon the IOP readings into two treatment groups of 12 animals each, establishing two substantially equivalent groups of animals according to average IOP. After randomizing the groups, test formulation was applied to the left eye and "vehicle" (formulation control) was applied into the contralateral eye (right) in respective animals. IOP was measured using a tonometer by personnel blind to the treatment groups at the following time points post treatment after topical treatment: 0.5, 1.0, 1.5, 2.0, 3.0, 4.0, 6.0, 8.0, 12.0, and 18.0 hours.

Results

All measured and presented values were expressed as Mean±SEM. Significance ($p<0.05$) as compared to vehicle was determined by unpaired t-test using Graph pad Prism version 6. Significant outliers were determined using Grubb's outlier test. Such identified outliers were not considered in calculations.

Results are shown in FIGS. 1-3. FIG. 1 illustrates the effect of LUMIGAN® 0.01% on intraocular pressure in the steroid-induced ocular hypertension rat model study. The graph of FIG. 1 represents the average IOP reading at each time point (0-18 hours). As described above, data is presented as mean±SEM, n=12 *$p<0.05$ versus vehicle compared with unpaired t-test. LUMIGAN® 0.01% showed a significant decrease compared to vehicle (control) in ocular pressure from 4-hour post administration until 12-hours post administration. A significant decrease in the average of 0.5-18-hour intraocular pressure was observed with LUMIGAN® 0.01% compared to vehicle (control) (see description of FIG. 3).

FIG. 2 shows the effect of Formulation A (low-BKC) on intraocular pressure in the steroid-induced ocular hypertension rat model study. The graph of FIG. 2 again represents the average IOP reading at each time point (0-18 hours) and the same statistical presentation applies. Formulation A (low-BKC) showed a significant decrease in ocular pressure compared to its respective vehicle at the 1, 2, 3, 6, 12, and 18-hour time points. A significant decrease in the average of 0.5-18-hour intraocular pressure was observed compared to vehicle for Formulation A (low-BKC) (see description of FIG. 3).

FIG. 3 represents the average percent decrease (between 0-18 hours) in intraocular pressure compared to each respective vehicle treatment of LUMIGAN® 0.01% and Formulation A (low-BKC). Data in FIG. 3 is presented in the same manner as described above. No statistically significant difference between the test formulations was observed when analyzed using standard statistical analysis (reduction in intraocular pressure observed with Formulation A was statistically comparable to that of LUMIGAN® 0.01%). LUMIGAN® 0.01% demonstrated a reduction in intraocular pressure compared to vehicle of 8%, while Formulation A demonstrated a reduction in intraocular pressure compared to vehicle of 10%, as illustrated in FIG. 3.

The intraocular pressure study data demonstrate that formulations of the invention, such as Formulation A (low-BKC), are capable of reducing intraocular pressure in a manner comparable to that of the on-market LUMIGAN® 0.01% product, and are capable of doing so with a significantly reduced concentration of benzalkonium chloride, while including a suitable secondary penetration enhancer, such as polysorbate 80 to enhance bimatoprost penetration.

EXEMPLARY ASPECTS OF THE INVENTION

The following is a non-limiting list of exemplary aspects, which is intended to highlight some of the various embodiments of the invention. Although presented in a numbered list format with cross-references, readers should note that these aspects (which are described a numbered paragraph of the specification) are not claims, but, rather, merely an alternative format for conveniently summarizing/describing aspects of the invention (this is clearly indicated by the fact that items described in this list are described as "aspects" and not "claims").

An ophthalmologically suitable composition comprising (a) about 0.005%-about 0.02% of a bimatoprost compound; (b) about 0.003-about 0.007% benzalkonium chloride, and (c) an effective amount of at least one secondary penetration enhancer that detectably enhances penetration of the bimatoprost into a mammalian eye, wherein an effective amount of the composition results in a reduction of intraocular pressure in a mammalian eye that is at least statistically comparable to the same amount of a composition comprising the same amount of bimatoprost compound and at least about 200% more benzalkonium chloride (aspect 1).

In one aspect, the invention provides a composition such as that described in aspect 1, wherein the at least one secondary penetration enhancer comprises at least one additional ophthalmologically suitable quaternary ammonium salt (aspect 2).

In one aspect, the invention provides a composition such as that described in aspect 2, wherein the at least one additional ophthalmologically suitable quaternary ammonium salt is benzethonium chloride, benzyltrimethylammonium chloride, lauryl trimethyl ammonium chloride, or a combination of two or all thereof (aspect 3).

In one aspect, the invention provides a composition such as that described in aspect 1, wherein the at least one secondary penetration enhancer is free of any quaternary ammonium salts (aspect 4).

In one aspect, the invention provides a composition such as that described in any one or more of aspects 1-4, wherein the at least one secondary penetration enhancer is characterizable as a nonionic surfactant and emulsifier, optionally clear in aqueous solution, optionally detectably or significantly non-irritating to ocular tissue, and capable of increasing the penetration of bimatoprost within ocular tissue, including any such compound modified in such a way that does not lead to a detectable or significant difference with respect to some, most, or generally all such characteristics with respect to an amount of polysorbate 80 that achieves a statistically similar level of penetration of bimatoprost (aspect 5).

In one aspect, the invention provides a composition such as that described in any one or more of aspects 1-5, wherein the at least one secondary penetration enhancer comprises one or more ophthalmologically suitable polyoxyethylene sorbitan fatty acid esters (aspect 6).

In one aspect, the invention provides a composition such as that described in any one or more of aspects 1-6, wherein the at least one secondary penetration enhancer makes up at least about 0.2% of the composition (aspect 7).

In one aspect, the invention provides a composition such as that described in any one or more of aspects 1-7, wherein the at least one secondary penetration enhancer makes up about 0.25%-about 2.5% of the composition (aspect 8).

In one aspect, the invention provides a composition such as that described in any one or more of aspects 1-8, wherein the at least one secondary penetration enhancer makes up at least about 0.5% of the composition (aspect 9).

In one aspect, the invention provides a composition such as that described in aspect 9, wherein the at least one secondary penetration enhancer makes up at least about 0.65% of the composition (aspect 10).

In one aspect, the invention provides a composition such as that described in aspect 10, wherein the at least one secondary penetration enhancer makes up at least about 0.85% of the composition (aspect 11).

In one aspect, the invention provides a composition such as that described in any one or more of aspects 6-11, wherein the polyoxyethylene sorbitan fatty acid esters comprise polysorbate 20, polysorbate 80, or a combination thereof (aspect 12).

In one aspect, the invention provides a composition such as that described in any one or more of aspects 6-12, wherein the polyoxyethylene sorbitan fatty acid esters makes up about 0.2% to about 2% of the composition (aspect 13).

In one aspect, the invention provides a composition such as that described in aspect 13, wherein the polyethylene sorbitan fatty acid esters make up at least about 0.5% of the composition (aspect 14).

In one aspect, the invention provides a composition such as that described in aspect 14, wherein the polyethylene sorbitan fatty acid esters make up at least about 0.85% of the composition (aspect 15).

In one aspect, the invention provides a composition such as that described in aspect 15, wherein the polyethylene sorbitan fatty acid esters make up at least about 1% of the composition (aspect 16).

In one aspect, the invention provides a composition such as that described in any one or more of aspects 12-16, wherein the polyoxyethylene sorbitan fatty acid ester primarily is composed of polysorbate 80 (aspect 17).

In one aspect, the invention provides a composition such as that described in aspect 17, wherein the polyoxyethylene sorbitan fatty acid ester primarily consists of or consists essentially of polysorbate 80 (aspect 18).

In one aspect, the invention provides a composition such as that described in any one or more of aspects 1-4, wherein the at least one secondary penetration enhancer comprises one or more ophthalmologically suitable nonionic surfactant having an HLB value of at least 14.5 (aspect 19).

In one aspect, the invention provides a composition such as that described in aspect 19, wherein the nonionic surfactant has an HLB value of at least 15.5 (aspect 20).

In one aspect, the invention provides a composition such as that described in aspect 20, wherein the nonionic surfactant has an HLB value of at least 16.5 (aspect 21).

In one aspect, the invention provides a composition such as that described in any one or more of aspects 1-4, wherein the secondary penetration enhancer is selected from a group comprising polyoxyl-n-castor oils (e.g., polyoxy-35-castor oil), polyarginine, polyserine, sesame seed oil, polyoxyl 40 stearate, tyloxapol (aspect 22).

In one aspect, the invention provides a composition such as that described in any one or more of aspects 1-4, wherein the secondary penetration enhancer is selected from a group comprising compounds characterizable as a polyoxyethylene (e.g., a polyoxyethylene glycol), polyoxypropylene (e.g., a polyoxyethylene glycol), a polyoxamine, or a block polymer comprising one or more polyoxyethylenes or (and/or) polyoxypropylenes (aspect 23).

In one aspect, the invention provides a composition such as that described in any one or more of aspects 1-23, wherein the composition further comprises a tertiary penetration enhancer (aspect 24).

In one aspect, the invention provides a composition such as that described in aspect 24, wherein the tertiary penetration enhancer is characterizable as a castor oil, such as a Cremophor or a polyoxyl-n-castor oil, such as polyoxy-35-castor oil (aspect 25).

In one aspect, the invention provides a composition such as that described in aspect 24, wherein the tertiary penetration enhancer comprises tocopherol polyethylene glycol succinate (TPGS) (aspect 26).

In one aspect, the invention provides a composition such as that described in aspect 24, wherein the tertiary penetration enhancer comprises tromethamine (tris) (aspect 27).

In one aspect, the invention provides a composition such as that described in any one or more of aspects 1-27, wherein the composition comprises between about 0.004-0.005% benzalkonium chloride (aspect 28).

In one aspect, the invention provides a composition such as that described in any one or more of aspects 1-28, wherein the composition comprises between about 0.0075-0.015% of a bimatoprost compound (aspect 29).

In one aspect, the invention provides a composition such as that described in aspect 29, wherein the composition comprises between about 0.009-0.011% of a bimatoprost compound (aspect 30).

In one aspect, the invention provides a composition such as that described in any one or more of aspects 1-30, wherein the composition is characterizable as lacking any one or more of glycerin, boric acid, sodium borate, benzododecinium bromide, sodium acetate, polyacrylate/carbomer, PVP/PVA, biguanide compound(s), amino acids including acylated amino acids, compounds characterizable as castor oils (including, e.g., Cremophors/Kolliphors), tocopherol polyethylene glycol succinate (TPGS), polyethylene sorbitan monolaurate, polyoxyethylene sorbitan monostearate, polyoxypropylene/polyoxyethylene block copolymers, polyoxypropylene/polyoxyethylene/ethylene diamine block copolymer, polyethylene glycols including polyethylene glycol hydroxystearate, sodium lauryl ether sulfate, sodium lauryl sarcosinate, laurylether sulfate triethanolamine propylene glycol, Texapon N40, polyoxyl-15-hydroxystearate, polyoxyl-35 castor oil, or polyethylene glycol 400 (aspect 31).

In another aspect, the invention provides a composition such as that described in any one or more of aspects 1-31, wherein the composition is a liquid solution (aspect 32).

In another aspect, the invention provides a composition such as that described in aspect 32, wherein the liquid solution is administered as drops to the mammalian eye (aspect 33).

In another aspect, the invention provides a composition such as that described in any one or more of aspects 1-33, wherein the composition exhibits a detectably or significantly greater reduction in intraocular pressure than LUMIGAN® 0.01% as measured 2 hours after administration to a mammalian eye (aspect 34).

In another aspect, the invention provides a composition such as that described in any one or more of aspects 1-34, wherein the composition exhibits a detectably or significantly greater reduction in intraocular pressure than LUMIGAN® 0.01% as measured about 4 hours after administration to a mammalian eye (aspect 35).

In another aspect, the invention provides a composition such as that described in any one or more of aspects 1-35, wherein the composition exhibits a detectably or significantly greater reduction in intraocular pressure than LUMIGAN® 0.01% as measured about 8 hours after administration to a mammalian eye (aspect 36).

In another aspect, the invention provides a composition such as that described in any one or more of aspects 1-36, wherein the composition exhibits a detectably or significantly greater reduction in intraocular pressure than LUMIGAN® 0.01% as measured about 12 hours after administration to a mammalian eye (aspect 37).

In another aspect, the invention provides a composition such as that described in any one or more of aspects 1-37, wherein the composition exhibits a detectably or significantly greater reduction in intraocular pressure than LUMIGAN® 0.01% as measured about 18 hours after administration to a mammalian eye (aspect 38).

In another aspect, the invention provides a composition such as that described in any one or more of aspects 35-38, wherein the composition reduces intraocular pressure in a mammalian eye suffering from increased intraocular pressure of at least 35% above normal by at least an average of about 1% more than LUMIGAN® 0.01% when measured in a statistically significant population of mammals in an appropriately powered and administered study (aspect 39).

In another aspect, the invention provides a composition such as that described in any one or more of aspects 1-39, wherein the composition reduces intraocular pressure in a mammalian eye suffering from increased intraocular pressure of at least 20% above normal, such as at least about 30% above normal, or a significant amount, by at least about 5%, such as at least about 8%, or other significant amount, when measured in a statistically significant population of mammals in an appropriately powered and administered study (aspect 40).

In another aspect, the invention provides a composition such as that described in any one or more of aspects 1-40, wherein the composition maintains the concentration of bimatoprost within 10% of that of the initial concentration of bimatoprost when stored up to at least 3 months at 40 degrees Celsius at 25% relative humidity, when stored up to at least 3 months at 25 degrees Celsius at 40% relative humidity, or both, when measured in an appropriately conducted stability study (aspect 41).

In another aspect, the invention provides a composition such as that described in any one or more of aspects 1-41, wherein the composition maintains the concentration of the bimatoprost impurity 15 (R) bimatoprost below 0.3% when stored for at least up to 3 months at 40 degrees Celsius and 25% relative humidity, when stored for up to at least 3 months at 25 degrees Celsius and 40% relative humidity, or both, when measured in an appropriately conducted stability study (aspect 42).

In another aspect, the invention provides a composition such as that described in any one or more of aspects 1-42, wherein the composition maintains the concentration of the bimatoprost impurity 15 keto bimatoprost below 0.7% when stored for at least up to 3 months at about 40 degrees Celsius and 25% relative humidity, when stored for up to at least 3 months at about 25 degrees Celsius and about 40% relative humidity, or both, when measured in an appropriately conducted stability study (aspect 43).

In another aspect, the invention provides a composition such as that described in any one or more of aspects 1-43, wherein the composition maintains the concentration of the bimatoprost impurity bimatoprost acid below about 0.5% when stored for at least up to 3 months at about 40 degrees Celsius and about 25% relative humidity, when stored for up to at least 3 months at about 25 degrees Celsius and about 40% relative humidity, or both, when measured in an appropriately conducted stability study (aspect 44).

In another aspect, the invention provides a composition such as that described in any one or more of aspects 1-44, wherein the composition maintains the concentration of unidentified bimatoprost impurities (e.g., at RRT 0.28) below about 0.3% when stored for at least up to about 3 months at 40 degrees Celsius (C) and 25% relative humidity, when stored for up to at least 3 months at about 25 degrees C. and about 40% relative humidity, or both when measured in an appropriately conducted stability study (aspect 45).

In one aspect, the invention provides a method of reducing elevated intraocular pressure in a mammal comprising administering an effective amount of an ophthalmologically suitable composition comprising (a) about 0.005%-about 0.02% of a bimatoprost compound; (b) about 0.003-about 0.007% benzalkonium chloride, and (c) an effective amount of at least one secondary penetration enhancer that detectably enhances penetration of the bimatoprost into a mammalian eye, wherein the administration of the composition results in a reduction of intraocular pressure in a mammalian eye that is at least statistically comparable to the same amount of a composition comprising the same amount of bimatoprost compound and at least about 200% more benzalkonium chloride (aspect 46).

In one aspect, the invention provides a method of treating a mammal suffering from an elevated intraocular pressure comprising administering to the mammal a composition comprising about 0.005%-about 0.02% of a bimatoprost compound; (a) about 0.003-about 0.007% benzalkonium chloride, and (b) an effective amount of at least one secondary penetration enhancer that detectably enhances penetration of the bimatoprost into a mammalian eye, wherein the administration of the composition reduces the intraocular pressure in the mammalian eye by an amount that is at least statistically comparable to the same amount of a composition comprising the same amount of bimatoprost compound and at least 200% more benzalkonium chloride (aspect 47).

In additional aspect, the invention provides a method such as that described in either or both of aspect 46 or aspect 47, wherein the at least one secondary penetration enhancer of the composition comprises at least one additional ophthalmologically suitable quaternary ammonium salt (aspect 48).

In additional aspect, the invention provides a method such as that described in aspect 48, wherein the at least one additional ophthalmologically suitable quaternary ammonium salt is benzethonium chloride, benzyltrimethylammonium chloride, lauryl trimethyl ammonium chloride, or a combination of two or all thereof (aspect 49).

In additional aspect, the invention provides a method such as that described in either or both of aspect 46 or aspect 47, wherein the at least one secondary penetration enhancer of the composition is free of any quaternary ammonium salts (aspect 50).

In additional aspect, the invention provides a method such as that described in any one or more of aspects 47-50, wherein the at least one secondary penetration enhancer of the composition is characterizable as a nonionic surfactant and emulsifier, clear in aqueous solution, non-irritating to ocular tissue, and capable of increasing the penetration of bimatoprost within ocular tissue, including any such compound modified in such a way that does not lead to a detectable or significant difference with respect to some, most, or generally all such characteristics with respect to an amount of polysorbate 80 that achieves a statistically similar level of penetration of the bimatoprost (aspect 51).

In additional aspect, the invention provides a method such as that described in any one or more of aspects 46-51, wherein the at least one secondary penetration enhancer of the composition comprises one or more ophthalmologically suitable polyoxyethylene sorbitan fatty acid esters (aspect 52).

In additional aspect, the invention provides a method such as that described in any one or more of aspects 47-52, wherein the at least one secondary penetration enhancer of the composition makes up at least about 0.2% of the composition (aspect 53).

In additional aspect, the invention provides a method such as that described in any one or more of aspects 46-53, wherein the at least one secondary penetration enhancer of the composition makes up about 0.25%-about 2.5% of the composition (aspect 54).

In another aspect, the invention provides a method such as that described in any one or more of aspects 46-54, wherein the at least one secondary penetration enhancer of the composition makes up at least about 0.5% of the composition (aspect 55).

In another aspect, the invention provides a method such as that described in aspect 55, wherein the at least one secondary penetration enhancer of the composition makes up at least about 0.65% of the composition (aspect 56).

In another aspect, the invention provides a composition such as that described in aspect 56, wherein the at least one secondary penetration enhancer of the composition makes up at least about 0.85% of the composition (aspect 57).

In another aspect, the invention provides a method such as that described in any one or more of aspects 52-57, wherein the polyoxyethylene sorbitan fatty acid esters of the composition comprise polysorbate 20, polysorbate 80, or a combination thereof (aspect 58).

In another aspect, the invention provides a method such as that described in any one or more of aspects 52-58, wherein the polyoxyethylene sorbitan fatty acid esters of the composition makes up about 0.2% to about 2% of the composition (aspect 59).

In another aspect, the invention provides a method such as that described in aspect 59, wherein the polyethylene sorbitan fatty acid esters of the composition make up at least about 0.5% of the composition (aspect 60).

In another aspect, the invention provides a method such as that described in aspect 60, wherein the polyethylene sorbitan fatty acid esters of the composition make up at least about 0.85% of the composition (aspect 61).

In another aspect, the invention provides a method such as that described in aspect 61, wherein the polyethylene sorbitan fatty acid esters of the composition make up at least about 1% of the composition (aspect 62).

In another aspect, the invention provides a method such as that described in any one or more of aspects 58-62, wherein the polyoxyethylene sorbitan fatty acid ester primarily is composed of polysorbate 80 (aspect 63).

In another aspect, the invention provides a method such as that described in aspect 63, wherein the polyoxyethylene sorbitan fatty acid ester primarily consists of or consists essentially of polysorbate 80 (aspect 64).

In another aspect, the invention provides a method such as that described in any one or more of aspects 46-50, wherein the at least one secondary penetration enhancer of the composition comprises one or more ophthalmologically suitable nonionic surfactant having an HLB value of at least 14.5 (aspect 65).

In another aspect, the invention provides a method such as that described in aspect 65, wherein the nonionic surfactant has an HLB value of at least 15.5 (aspect 66).

In another aspect, the invention provides a method such as that described in aspect 66, wherein the nonionic surfactant has an HLB value of at least 16.5 (aspect 67).

In another aspect, the invention provides a method such as that described in any one or more of aspects 46-50, wherein the secondary penetration enhancer of the composition is selected from a group comprising polyoxyl-n-castor oils (e.g., polyoxy-35-castor oil), polyarginine, polyserine, sesame seed oil, polyoxyl 40 stearate, tyloxapol (aspect 68).

In another aspect, the invention provides a method such as that described in any one or more of aspects 46-50, wherein the secondary penetration enhancer of the composition is selected from a group comprising compounds characterizable as a polyoxyethylene (e.g., a polyoxyethylene glycol), polyoxypropylene (e.g., a polyoxyethylene glycol), a polyoxamine, or a block polymer comprising one or more polyoxyethylenes and/or polyoxypropylenes (aspect 69).

In another aspect, the invention provides a method such as that described in any one or more of aspects 46-69, wherein the composition further comprises a tertiary penetration enhancer (aspect 70).

In another aspect, the invention provides a method such as that described in aspect 70, wherein the tertiary penetration enhancer of the composition is characterizable as a castor oil, such as a Cremophor or a polyoxyl-n-castor oil, such as polyoxy-35-castor oil (aspect 71).

In another aspect, the invention provides a method such as that described in aspect 70, wherein the tertiary penetration enhancer of the composition comprises tocopherol polyethylene glycol succinate (TPGS) (aspect 72).

In another aspect, the invention provides a method such as that described in aspect 70, wherein the tertiary penetration enhancer of the composition comprises tromethamine (tris) (aspect 73).

In another aspect, the invention provides a method such as that described in any one or more of aspects 46-73, wherein the composition comprises between about 0.004-0.005% benzalkonium chloride (aspect 74).

In another aspect, the invention provides a method such as that described in any one or more of aspects 46-74, wherein the composition comprises between about 0.0075-0.015% of a bimatoprost compound (aspect 75).

In another aspect, the invention provides a method such as that described in aspect 75, wherein the composition comprises between about 0.009-0.011% of a bimatoprost compound (aspect 76).

In another aspect, the invention provides a method such as that described in any one or more of aspects 46-76; wherein the composition is characterizable as lacking any one or more of glycerin, boric acid, sodium borate, benzododecinium bromide, sodium acetate, polyacrylate/carbomer, PVP/PVA, biguanide compound(s), amino acids including acylated amino acids, compounds characterizable as castor oils (including, e.g., Cremophors/Kolliphors), tocopherol polyethylene glycol succinate (TPGS), polyethylene sorbitan monolaurate, polyoxyethylene sorbitan monostearate, polyoxypropylene/polyoxyethylene block copolymers, polyoxypropylene/polyoxyethylene/ethylene diamine block copolymer, polyethylene glycols including polyethylene glycol hydroxystearate, sodium lauryl ether sulfate, sodium lauryl sarcosinate, laurylether sulfate triethanolamine propylene glycol, Texapon N40, polyoxyl-15-hydroxystearate, polyoxyl-35 castor oil, or polyethylene glycol 400 (aspect 77).

In another aspect, the invention provides a method such as that described in any one or more of aspects 46-77, wherein the composition is a liquid solution (aspect 78).

In another aspect, the invention provides a method such as that described in aspect 78, wherein the liquid solution is administered as drops to the mammalian eye (aspect 79).

In another aspect, the invention provides a method such as that described in any one or more of aspects 46-79, wherein application of the method results in a detectably or significantly greater reduction in intraocular pressure than that obtained by use of LUMIGAN® 0.01% as measured 2 hours after administration to a mammalian eye (aspect 80).

In another aspect, the invention provides a method such as that described in any one or more of aspects 46-80, wherein application of the method results in a detectably or significantly greater reduction in intraocular pressure than that obtained by use of LUMIGAN® 0.01% as measured 4 hours after administration to a mammalian eye (aspect 81).

In another aspect, the invention provides a method such as that described in any one or more of aspects 46-81, wherein the application of the method results in a detectably or significantly greater reduction in intraocular pressure than that obtained by use of LUMIGAN® 0.01% as measured 8 hours after administration to a mammalian eye (aspect 82).

In another aspect, the invention provides a method such as that described in any one or more of aspects 46-82, wherein the application of the method results in a detectably or significantly greater reduction in intraocular pressure than that obtained by use of LUMIGAN® 0.01% as measured 12 hours after administration to a mammalian eye (aspect 83).

In another aspect, the invention provides a method such as that described in any one or more of aspects 46-83, wherein the application of the method results in a detectably or significantly greater reduction in intraocular pressure than that obtained by use of LUMIGAN® 0.01% as measured 18 hours after administration to a mammalian eye (aspect 84).

In another aspect, the invention provides a method such as that described in any one or more of aspects 80-84, wherein application of the method results in a reduction in intraocular pressure in a mammalian eye suffering from increased intraocular pressure of at least 35% above normal by at least an average of about 1% more than use of LUMIGAN® 0.01% when measured in a statistically significant population of mammals in an appropriately powered and administered study (aspect 85).

In another aspect, the invention provides a method such as that described in any one or more of aspects 46-85, wherein application of the method results in a reduction in intraocular pressure in a mammalian eye suffering from increased intraocular pressure of at least 30% above normal by at least about 8% when measured in a statistically significant population of mammals in an appropriately powered and administered study (aspect 86).

In another aspect, the invention provides a method such as that described in any one or more of aspects 46-86, wherein the composition maintains the concentration of bimatoprost within 10% of that of the initial concentration of bimatoprost when stored up to at least 3 months at 40 degrees Celsius at 25% relative humidity, when stored up to at least 3 months at 25 degrees Celsius at 40% relative humidity, or both, when measured in an appropriately conducted stability study (aspect 87).

In another aspect, the invention provides a method such as that described in any one or more of aspects 46-87, wherein the composition maintains the concentration of the bimatoprost impurity 15 (R) bimatoprost below 0.3% when stored for at least up to 3 months at 40 degrees Celsius and 25% relative humidity, when stored for up to at least 3 months at 25 degrees Celsius and 40% relative humidity, or both, when measured in an appropriately conducted stability study (aspect 88).

In another aspect, the invention provides a method such as that described in any one or more of aspects 46-88, wherein the composition maintains the concentration of the bimatoprost impurity 15 keto bimatoprost below 0.7% when stored for at least up to about 3 months at about 40 degrees Celsius and about 25% relative humidity, when stored for up to at least about 3 months at about 25 degrees Celsius and 40% relative humidity, or both, when measured in an appropriately conducted stability study (aspect 89).

In another aspect, the invention provides a method such as that described in any one or more of aspects 46-89, wherein the composition maintains the concentration of the bimatoprost impurity bimatoprost acid below about 0.5% when stored for at least up to about 3 months at about 40 degrees Celsius and about 25% relative humidity, when stored for up to at least about 3 months at about 25 degrees Celsius and about 40% relative humidity, or both, when measured in an appropriately conducted stability study (aspect 90).

In another aspect, the invention provides a method such as that described in any one or more of aspects 46-90, wherein the composition maintains the concentration of unidentified bimatoprost impurities at RRT 0.28 below 0.3% when stored for at least up to about 3 months at about 40 degrees Celsius and about 25% relative humidity, when stored for up to at least about 3 months at about 25 degrees Celsius and 40% relative humidity, or both when measured in an appropriately conducted stability study (aspect 91).

In one aspect, the invention provides an ophthalmic composition comprising from about 0.005% to 0.02% bimatoprost by weight, 50-ppm or less of benzalkonium chloride, a penetration enhancer or solubilizer, and one or more pharmaceutically acceptable excipients (aspect 92).

In a further aspect, the invention provides an ophthalmic composition such as that described in aspect 92, wherein the penetration enhancer or solubilizer is polysorbate-80, tocopherol polyethylene glycol succinate (TPGS), polyoxyl castor oil, poly-arginine, poly-cerine, tromethamine (tris), or sesame seed oil, alone or in combination (aspect 93).

In a further aspect, the invention provides an ophthalmic composition such as that described in aspect 92, wherein the composition consists essentially of about 0.01% bimatoprost, 50 ppm or less of benzalkonium chloride, a penetration enhancer or solubilizer, a phosphate buffer, sodium chloride, and water (aspect 94).

In a further aspect, the invention provides an ophthalmic composition such as that described in aspect 92, wherein the composition consists of about 0.01% bimatoprost, 50 ppm or less of benzalkonium chloride, a penetration enhancer or solubilizer, a phosphate buffer, sodium chloride, and water (aspect 95).

In one aspect, the invention provides a process for preparation of ophthalmic composition comprising from 0.005% to 0.02% bimatoprost by weight, 50 ppm or less of benzalkonium chloride, and one or more pharmaceutically acceptable excipients, wherein the composition is sterilized by using one or more methods selected from heat sterilization, gaseous sterilization, filtration sterilization or radiation sterilization (aspect 96).

Exemplary Formulations and Methods of Production/Manufacture Thereof

To further exemplify aspects of the invention, a group of specific exemplary formulations are provided here, along with suitable methods to produce such formulations. These exemplary formulations specifically comprise about 0.005-about 0.02% bimatoprost and about 50 ppm of benzalkonium chloride and one or more solubilizer/penetration enhancer(s), illustrative of those described herein. As such formulations are exemplary embodiments only they should in no way be construed as limiting the scope of the disclosure/invention.

Formulation I and Production Thereof

Formulations according to Table 5 can be successfully prepared according to the following procedure:

TABLE 5

Composition with polysorbate-80 as solubilizer/penetration enhancer

| Sr. No | Name of ingredients | Percentage (w/v) in composition |
| --- | --- | --- |
| 1 | Bimatoprost | 0.005-0.02 |
| 2 | Polysorbate-80 | 0.5-2 |
| 3 | Benzalkonium chloride | 0.005 |
| 4 | Sodium chloride | 0.2-0.8 |
| 5 | Dibasic sodium phosphate | 0.1-0.3 |
| 6 | Citric acid monohydrate | 0.005-0.1 |
| 7 | Sodium hydroxide | q.s. to adjust pH 7.10 to 7.30 |
| 8 | Hydrochloric acid | q.s. to adjust pH 7.10 to 7.30 |
| 9 | Water for Injection | q.s. to 1 mL |
| 10 | Nitrogen NF | NA |

Procedure, Part I:

1. 1.1 times the quantity of water for injection (WFI) required for production ("batch quantity") is obtained in a suitable, primary ("main") container and heated.

2. 10% of the batch quantity of hot WFI is transferred to a first suitable container.

3. The hot WFI in the first container is purged with nitrogen.

4. The WFI is cooled with nitrogen purging to room temperature, and polysorbate 80 is added.

5. The mixture is stirred until the polysorbate 80 is completely dissolved.

6. The benzalkonium chloride is added to the solution while stirring.

7. Oxygen levels are monitored; once the oxygen level drops below 2 ppm, the bimatoprost is added to the solution.

8. The solution is stirred until the bimatoprost is completely dissolved.

Procedure, Part II:

9. In the main container, hot WFI is purged with nitrogen and cooled to room temperature.

10. Once at room temperature, 15% of the cooled nitrogen purged water is transferred into a second, small container, to be used for volume adjustment. Nitrogen purging is continued in this small container. In the main container once the temperature of the WFI reaches room temperature and the oxygen level is below 2 ppm, sodium chloride, dibasic sodium phosphate and citric acid are added one after another, ensuring that the previous ingredient is in solution before addition of the next ingredient.

11. After the complete dissolution of the above ingredients, the pH of the solution is adjusted to be between 7.1 to 7.3 using sodium hydroxide and/or hydrochloric acid.

12. The contents of the container of Part I are transferred to the container of Part II and are stirred sufficiently to form a uniform solution.

13. The solution is brought to a volume using the remaining WFI from the small container.

14. The solution is filtered through a sterilizing grade, 0.22µ filter and transferred to a buffer tank.

15. From the buffer tank, the solution is filled into appropriate bottles.

Formulation II and Production Thereof

Formulations according to Table 6 can be successfully prepared according to the following procedure:

TABLE 6

Composition with TPGS as solubilizer/penetration enhancer

| Sr. No | Name of ingredients | Percentage (w/v) in composition |
| --- | --- | --- |
| 1 | Bimatoprost | 0.005-0.02 |
| 2 | Tocopherol Polyethylene Glycol Succinate | 0.5-2 |
| 3 | Benzalkonium chloride | 0.005 |
| 4 | Sodium chloride | 0.2-0.8 |
| 5 | Dibasic sodium phosphate | 0.1-0.3 |
| 6 | Citric acid monohydrate | 0.005-0.1 |
| 7 | Sodium hydroxide | q.s. to adjust pH 7.10 to 7.30 |
| 8 | Hydrochloric acid | q.s. to adjust pH 7.10 to 7.30 |
| 9 | Water for Injection | q.s. to 1 mL |
| 10 | Nitrogen NF | NA |

Procedure, Part I:

1. 1.1 times the quantity of water for injection (WFI) required for production ("batch quantity") is obtained in a suitable, primary ("main") container and heated.

2. 10% of the batch quantity of hot WFI is transferred to a first suitable container.

3. The hot WFI in the first container is purged with nitrogen.

4. The WFI is cooled with nitrogen purging to room temperature and tocopherol polyethylene glycol succinate (TPGS) is added.

5. The mixture is stirred until the TPGS is completely dissolved.

6. The benzalkonium chloride is added to the solution while stirring.

7. Oxygen levels are monitored; once the oxygen level drops below 2 ppm, the bimatoprost is added to the solution.

8. The solution is stirred until the bimatoprost is completely dissolved.

Procedure, Part II:

9. In the main container, hot WFI is purged with nitrogen and cooled to room temperature.

10. Once at room temperature, 15% of the cooled nitrogen purged water is transferred into a second, small container, to be used for volume adjustment. Nitrogen purging is continued in this small container.

11. In the main container once the temperature of the WFI reaches room temperature and the oxygen level is below 2 ppm, sodium chloride, dibasic sodium phosphate and citric acid are added, one after another, ensuring that the previous ingredient is in solution before addition of the next ingredient.

12. After the complete dissolution of the above ingredients, the pH of the solution is adjusted to be between 7.1 to 7.3 using sodium hydroxide and/or hydrochloric acid.

13. The contents of the container of Part I are transferred to the container of Part II and are stirred sufficiently to form a uniform solution.

14. The solution is brought to a volume using the remaining WFI from the small container.

15. The solution is filtered through a sterilizing grade, 0.22p filter and transferred to a buffer tank.

16. From the buffer tank, the solution is filled into appropriate bottles.

Formulation III and Production Thereof

Formulations according to Table 7 can be successfully prepared according to the following procedure:

TABLE 7

Composition with Polyoxyl 35 castor oil as solubilizer/penetration enhancer.

| Sr. No | Name of ingredients | Percentage (w/v) in composition |
| --- | --- | --- |
| 1 | Bimatoprost | 0.005-0.02 |
| 2 | Polyoxyl 35 castor oil (Cremophor EL) | 0.5-2 |
| 3 | Benzalkonium chloride | 0.005 |
| 4 | Sodium chloride | 0.2-0.8 |
| 5 | Dibasic sodium phosphate | 0.1-0.3 |
| 6 | Citric acid monohydrate | 0.005-0.1 |
| 7 | Sodium hydroxide | q.s. to adjust pH 7.10 to 7.30 |
| 8 | Hydrochloric acid | q.s. to adjust pH 7.10 to 7.30 |
| 9 | Water for Injection | q.s. to 1 mL |
| 10 | Nitrogen NF | NA |

Procedure, Part I:

1. 1.1 times the quantity of water for injection (WFI) required for production ("batch quantity") is obtained in a suitable, primary ("main") container and heated.

2. 10% of the batch quantity of hot WFI is transferred to a first suitable container.

3. The hot WFI in the first container is purged with nitrogen.

4. The WFI is cooled with nitrogen purging to room temperature and Polyoxyl 35 castor oil (Cremophor EL) is added.

5. The mixture is stirred until the Cremophor EL is completely dissolved.

6. The benzalkonium chloride is added to the solution while stirring.

7. Oxygen levels are monitored; once the oxygen level drops below 2 ppm, the bimatoprost is added to the solution.

8. The solution is stirred until the bimatoprost is completely dissolved.

Procedure, Part II:

9. In the main container, hot WFI is purged with nitrogen and cooled to room temperature.

10. Once at room temperature, 15% of the cooled nitrogen purged water is transferred into a second, small container, to be used for volume adjustment. Nitrogen purging is continued in this small container.

11. In the main container once the temperature of the WFI reaches room temperature and the oxygen level is below 2 ppm, sodium chloride, dibasic sodium phosphate and citric acid are added, one after another, ensuring that the previous ingredient is in solution before addition of the next ingredient.

12. After the complete dissolution of the above ingredients, the pH of the solution is adjusted to be between 7.1 to 7.3 using sodium hydroxide and/or hydrochloric acid.

13. The contents of the container of Part I are transferred to the container of Part II and are stirred sufficiently to form a uniform solution.

14. The solution is brought to a volume using the remaining WFI from the small container.

15. The solution is filtered through a sterilizing grade, 0.22p filter and transferred to a buffer tank.

16. From the buffer tank, the solution is filled into appropriate bottles.

Formulation IV

Formulations according to Table 8 were successfully prepared according to the following procedure:

TABLE 8

Composition with Polysorbate-80, TPGS and Polyoxyl 35 castor oil as solubilizer and/penetration enhancer

| Sr. No | Name of ingredients | Percentage (w/v) in composition |
| --- | --- | --- |
| 1 | Bimatoprost | 0.005-0.02 |
| 2 | One or more of polysorbate-80, TPGS and Polyoxyl 35 castor oil (Cremophor EL) | 0.5-2 |
| 3 | Benzalkonium chloride | 0.005 |
| 4 | Sodium chloride | 0.2-0.8 |
| 5 | Dibasic sodium phosphate | 0.1-0.3 |
| 6 | Citric acid monohydrate | 0.005-0.1 |
| 7 | Sodium hydroxide | q.s. to adjust pH 7.10 to 7.30 |
| 8 | Hydrochloric acid | q.s. to adjust pH 7.10 to 7.30 |
| 9 | Water for Injection | q.s. to 1 mL |
| 10 | Nitrogen NF | NA |

Procedure, Part I:

1. 1.1 times the quantity of water for injection (WFI) required for production ("batch quantity") is obtained in a suitable, primary ("main") container and heated.

2. 10% of the batch quantity of hot WFI is transferred to a first suitable container.

3. The hot WFI in the first container is purged with nitrogen.

4. The WFI is cooled with nitrogen purging to room temperature and Polysorbate 80, TPGS, and Polyoxyl 35 castor oil (Cremophor EL) are added.

5. The mixture is stirred until the solubilizers are completely dissolved.

6. The benzalkonium chloride is added to the solution while stirring.

7. Oxygen levels are monitored; once the oxygen level drops below 2 ppm, the bimatoprost is added to the solution.

8. The solution is stirred until the bimatoprost is completely dissolved.

Procedure, Part II:

9. In the main container, hot WFI is purged with nitrogen and cooled to room temperature.

10. Once at room temperature, 15% of the cooled nitrogen purged water is transferred into a second, small container, to be used for volume adjustment. Nitrogen purging is continued in this small container.

11. In the main container once the temperature of the WFI reaches room temperature and the oxygen level is below 2 ppm, sodium chloride, dibasic sodium phosphate and citric acid are added one after another, ensuring that the previous ingredient is in solution before addition of the next ingredient.

12. After the complete dissolution of the above ingredients, the pH of the solution is adjusted to be between 7.1 to 7.3 using sodium hydroxide and/or hydrochloric acid.

13. The contents of the container of Part I are transferred to the container of Part II and are stirred sufficiently to form a uniform solution.

14. The solution is brought to a volume using the remaining WFI from the small container.

15. The solution is filtered through a sterilizing grade, 0.22 μm filter and transferred to a buffer tank.

16. From the buffer tank, the solution is filled into appropriate bottles.

The invention claimed is:

1. An ophthalmologically suitable eye drop formulation comprising (a) 0.005%-0.02% of a bimatoprost compound, (b) 0.003%-0.007% benzalkonium chloride, and (c) 0.75%-2.5% of a penetration enhancer component comprising one or more ophthalmologically suitable polyoxyethylene sorbitan fatty acid esters, wherein (d) the formulation does not comprise a polyacrylate polymer, a component having an HLB value greater than 17.5, or both, and (e) the ratio of the one or more ophthalmologically suitable polyoxyethylene sorbitan fatty acid esters to the benzalkonium chloride is between 107:1 and 833:1.

2. The ophthalmologically suitable eye drop formulation of claim 1, wherein the formulation is free of any quaternary ammonium salts other than the benzalkonium chloride.

3. The ophthalmologically suitable eye drop formulation of claim 2, wherein the formulation comprises 0.004%-0.005% benzalkonium chloride.

4. The ophthalmologically suitable eye drop formulation of claim 3, wherein the composition comprises 0.009%-0.011% of a bimatoprost compound.

5. The ophthalmologically suitable eye drop formulation of claim 4, wherein the one or more polyethylene sorbitan fatty acid esters make up at least 0.85% of the ophthalmologically suitable eye drop formulation.

6. The ophthalmologically suitable eye drop formulation of claim 5, wherein the one or more polyethylene sorbitan fatty acid esters comprise polysorbate 20, polysorbate 80, or a combination thereof.

7. The ophthalmologically suitable eye drop formulation of claim 2, wherein the formulation comprises at least one secondary penetration enhancer component that comprises castor oil.

8. The ophthalmologically suitable eye drop formulation of claim 6, wherein the formulation comprises at least one secondary penetration enhancer component that comprises castor oil.

9. The ophthalmologically suitable eye drop formulation of claim 6, wherein the one or more polyoxyethylene sorbitan fatty acid esters consists essentially of polysorbate 80.

10. The ophthalmologically suitable eye drop formulation of claim 9, wherein the formulation comprises at least one secondary penetration enhancer that comprises castor oil.

11. The ophthalmologically suitable eye drop formulation of claim 1, wherein the formulation is free of polyoxyl-15-hydroxystearate.

12. The ophthalmologically suitable eye drop formulation of claim 1, wherein the penetration enhancer component predominately comprises polysorbate 20, polysorbate 80, or a combination thereof.

13. The ophthalmologically suitable eye drop formulation of claim 1, wherein the ratio of the one or more ophthalmologically suitable polyoxyethylene sorbitan fatty acid esters to the benzalkonium chloride is greater than 250:1.

* * * * *